US009308245B2

(12) United States Patent
Poe, III et al.

(10) Patent No.: US 9,308,245 B2
(45) Date of Patent: Apr. 12, 2016

(54) SPRAY DRIED COMPOSITIONS AND METHODS OF USE

(71) Applicant: Life-Science Innovations, LLC, Willmar, MN (US)

(72) Inventors: Bobby Gene Poe, III, Willmar, MN (US); Jared Randall Huisinga, Pennock, MN (US)

(73) Assignee: LIFE-SCIENCE INNOVATIONS, LLC, Willmar, MN (US)

( * ) Notice: Subject to any disclaimer, the term of this patent is extended or adjusted under 35 U.S.C. 154(b) by 0 days.

(21) Appl. No.: 14/270,794

(22) Filed: May 6, 2014

(65) Prior Publication Data

US 2014/0242116 A1 Aug. 28, 2014

Related U.S. Application Data

(62) Division of application No. 13/771,936, filed on Feb. 20, 2013, now Pat. No. 8,753,643.

(60) Provisional application No. 61/622,777, filed on Apr. 11, 2012.

(51) Int. Cl.
| | |
|---|---|
| *A61K 39/00* | (2006.01) |
| *A61K 39/02* | (2006.01) |
| *A61K 39/112* | (2006.01) |
| *B01D 1/18* | (2006.01) |

(52) U.S. Cl.
CPC ............. *A61K 39/02* (2013.01); *A61K 39/0275* (2013.01); *B01D 1/18* (2013.01); *A61K 2039/552* (2013.01); *A61K 2039/55505* (2013.01); *A61K 2039/55555* (2013.01); *A61K 2039/55577* (2013.01)

(58) Field of Classification Search

CPC ...................................................... A61K 39/02

See application file for complete search history.

(56) References Cited

U.S. PATENT DOCUMENTS

| | | | | |
|---|---|---|---|---|
| 3,887,699 | A | 6/1975 | Yolles | |
| 4,164,560 | A | 8/1979 | Folkman et al. | |
| 4,326,523 | A | 4/1982 | Wolfrom et al. | |
| 4,452,775 | A | 6/1984 | Kent | |
| 4,767,628 | A | 8/1988 | Hutchinson | |
| 4,863,735 | A | 9/1989 | Kohn et al. | |
| 4,938,763 | A | 7/1990 | Dunn et al. | |
| 5,324,519 | A | 6/1994 | Dunn et al. | |
| 5,346,891 | A * | 9/1994 | Soma et al. | 514/54 |
| 5,830,479 | A | 11/1998 | Emery et al. | |
| 6,077,543 | A | 6/2000 | Gordon et al. | |
| 6,432,412 | B1 | 8/2002 | Emery et al. | |
| 7,138,124 | B2 | 11/2006 | Emery et al. | |
| 7,160,549 | B2 | 1/2007 | Emery et al. | |
| 7,449,201 | B2 | 11/2008 | Hastedt et al. | |
| 2005/0095682 | A1 | 5/2005 | Straub et al. | |
| 2005/0186217 | A1 | 8/2005 | Emery et al. | |
| 2005/0191246 | A1 | 9/2005 | Bechtold-Peters et al. | |
| 2006/0083753 | A1 | 4/2006 | Straub et al. | |
| 2006/0269564 | A1 | 11/2006 | Emery et al. | |

FOREIGN PATENT DOCUMENTS

| | | | |
|---|---|---|---|
| WO | WO 96/32149 | A1 | 10/1996 |
| WO | WO 97/41833 | A1 | 11/1997 |
| WO | WO 2010/111273 | A1 | 9/2010 |

OTHER PUBLICATIONS

Abdul-Fattah et al., "Drying-Induced Variations in Physico-Chemical Properties of Amorphous Pharmaceuticals and Their Impact on Stability II: Stability of a Vaccine" *Pharmaceutical Research*, Apr. 2007; 24(4):715-727.

Amorij et al., "Development of Stable Influenza Vaccine Powder Formulations; Challenges and Possibilities" *Pharmaceutical Research*, Jun. 2008; 25(6):1256-1273.

Balan et al., "Orally Administered Ovine Serum Immunoglobulins Influence Growth Performance, Organ Weights, and Gut Morphology in Growing Rats" *The Journal of Nutrition*, Feb. 2009; 139(2):244-249 Online: Dec. 23, 2008.

Baras et al., "Parameters Influencing the Antigen Release from Spray-Dried Poly(DL-lactide) Microparticles" *International Journal of Pharmaceutics*, 2000; 200:133-145.

Cal and Sollohub, "Spray Drying Technique. I: Hardware and Process Parameters" *Journal of Pharmaceutical Sciences*, Feb. 2010; 99(2):575-586 Online: Sep. 22, 2009.

Chen et al., "Thermostable Formulations of a Hepatitis B Vaccine and a Meningitis A Polysaccharide Conjugate Vaccine Produced by a Spray Drying Method" *Vaccine*, Apr. 2010; 28:5093-5099 Online May 15, 2010.

Corbanie et al., "Vaccination of Broiler Chickens with Dispersed Dry Powder Vaccines as an Alternative for Liquid Spray and Aerosol Vaccination" *Vaccine*, 2008; 26:4469-4476 Online: Jul. 1, 2008.

Coulton and Braun, "Protein II Influences Ferrichrome-Iron Transport in *Escherichia coli* k12" *Journal of General Microbiology*, 1979; 110:211-220.

Courcol et al., "Siderophore Production by *Staphylococcus aureus* and Identification of Iron-Regulated Proteins" *Infection and Immunity*, May 1997; 65(5):1944-1948.

(Continued)

*Primary Examiner* — Albert Navarro
(74) *Attorney, Agent, or Firm* — Mueting, Raasch & Gebhardt, P.A.

(57) ABSTRACT

Provided herein are insoluble particles that include polypeptides. The polypeptides may have immunogenicity that is greater than the immunogenicity of the same polypeptides when they are not present in the particle. The polypeptides may be soluble before incorporation into the particles and insoluble after incorporation into the particles. The particles may include lipopolysaccharide, wherein the lipopolysaccharide is insoluble. The particles may include a carrier. In one embodiment, a carrier is present at no greater than 0.001 mg carrier/mg particles. In one embodiment, a carrier is present at a ratio of carrier to polypeptide (weight:weight) of no greater than 0.05:1. In one embodiment, a carrier is not detectable in the particles.

25 Claims, 6 Drawing Sheets

(56) References Cited

OTHER PUBLICATIONS

Crosa, "Genetics and Molecular Biology of Siderophore-Mediated Iron Transport in Bacteria" *Microbiological Review*, Dec. 1989; 53(4):517-530.

E-TOXATE® Technical Bulletin No. 210. SIGMA Chemical Company: St. Louis, Mo. Copyright 2000. Available on the Internet:<URL:http://www.sigmaaldrich.com/content/dam/sigma-aldrich/docs/Sigma/Bulletin/210sebul.pdf>; 4 pgs.

Erdei et al., "Lactoferrin Binds to Porins OmpF, and OmpC in *Escherichia coli*" *Infection and Immunity*, Apr. 1994; 62(4):1236-1240.

Harlow and Lane (Eds.), *Antibodies, A Laboratory Manual*, New York, NY 1988. Cold Spring Harbor Laboratory Press; Cover page, publisher's page, and Chapter 5 (94 pgs).

Jin et al., "Stabilizing Formulations for Inhalable Powders of an Adenovirus 35-vectored Tuberculosis (TB) Vaccine (AERAS-402)" *Vaccine*, 2010; 28:4369-4375 Online: May 2, 2010.

Keler and Nowotny, "Metachromatic Assay for the Quantitative Determination of Bacterial Endotoxins" *Analytical Biochemistry*, Jul. 1986; 156(1):189-193.

Kohn et al., "Single-Step Immunization Using a Controlled Release Biodegradable Polymer with Sustained Adjuvant Activity" *Journal of Immunological Methods*, Dec. 4, 1986; 95(1)31-38.

Kristensen and Chen, "Stabilization of Vaccines: Lesson Learned" *Human Vaccines*, Mar. 17, 2010; 6(3): 229-231.

Maa et al., "The Effect of Operating and Formulation Variables on the Morphology of Spray-Dried Protein Particles" *Pharmaceutical Development and Technology*, Aug. 1997; 2(3):213-223.

Maa et al., "Spray-Drying of Air-Liquid Interface Sensitive Recombinant Human Growth Hormone" *Journal of Pharmaceutical Sciences*, Feb. 1998; 87(2):152-159.

Maa et al., "Stabilization of Alum-Adjuvanted Vaccine Dry Powder Formulations: Mechanism and Application" *Journal of Pharmaceutical Sciences*, Feb. 2003; 92(2):319-332.

Maa et al., "Hepatitis-B Surface Antigen (HBsAg) Powder Formulation: Process and Stability Assessment" *Current Drug Delivery*, 2007; 4(1):57-67.

Magalhaes et al., "Methods of Endotoxin Removal from Biological Preparations: a Review" *Journal of Pharmacy and Pharmaceutical Sciences*, 2007; 10(3):388-404.

Masters, *Spray Drying Handbook*, 5th edition, New York, NY 1991. John Wiley and Sons; Cover page, publisher's page, and table of contents (7 pgs).

Muir et al., "Immunity, Vaccination and the Avian Intestinal Tract" *Developmental and Cooperative Immunology*, 2000; 24:325-342.

Nguyen et al., "Protein Powders for Encapsulation: A Comparison of Spray-Freeze Drying and Spray Drying of Darbepoetin Alfa" *Pharmaceutical Research*, Mar. 2004; 21(3):507-514.

Nikaido and Vaara, "Outer Membrane", in *Escherichia coli* and *Salmonella typhimurium, Cellular and Molecular Biology*, Neidhardt et al., (eds.), Washington, D.C. 1987. American Society for Microbiology; Cover page, publisher's page, table of contents, and Chapter 5 (35 pages).

O'Hagan (Ed.), *Vaccine Adjuvants: Preparation Methods and Research Protocols*, Totowa, New Jersey 2000. Humana Press, Inc.; Cover page, publisher's page, and pp. 74-75.

Ohtake et. al, "Heat-Stable Measles Vaccine Produced by Spray Drying" *Vaccine*, 2010; 28:1275-1284 Online: Nov, 25, 2009.

Saluja et al., "A Comparison Between Spray Drying and Spray Freeze Drying to Produce an Influenza Subunit Vaccine Powder for Inhalation" *Journal of Controlled Release*, Feb. 25, 2010; 144:127-133.

Slowinska et al., "Isolation, Characterization and cDNA Sequencing of Acrosin from Turkey-Spermatozoa" *Comparative Biochemisty and Physiology, Part B*, 2010; 157:127-136 Online Jun. 1, 2010.

Sollohub and Cal, "Spray Drying Technique: II. Current Applications in Pharmaceutical Technology" *Journal of Pharmaceutical Sciences*, Feb. 2010; 99(2):587-597 Online Oct. 27, 2009.

Watson et al., eds. *Endotoxins and Their Detection With the Limulus Amebocyte Lysate Test*, Alan R. Liss, Inc. 150 5th Avenue, New York, 1982; Cover page, publisher's page, and table of contents only (5 pgs).

* cited by examiner

SPRAY DRIED COMPOSITIONS AND METHODS OF USE

CROSS-REFERENCE TO RELATED APPLICATIONS

This application is a divisional of patent application Ser. No. 13/771,936, filed Feb. 20, 2013, (pending), which claims the benefit of U.S. Provisional Application Ser. No. 61/622,777, filed Apr. 11, 2012, which are incorporated by reference herein.

BACKGROUND

It is often desirable to store immunologically active antigens in a dry form to increase shelf-life. In order to accomplish this, the aqueous antigens must be dehydrated in a manner that preserves their antigenicity. Conventional methods for preserving antigenic materials from sensitive biological samples include freeze drying, spray drying, spray freeze drying and foam drying. Dehydrating an antigen usually results in a highly soluble powder, which can be rehydrated at the time of use.

Carrier molecules are conventionally added to the aqueous preparations prior to dehydration to protect the sensitive biological samples from thermal and mechanical degradation during the drying process. These carriers have been necessary to preserve the biological activity and antigenicity of the dehydrate product (Maa et al., 2007, Current Drug Delivery, 4:57-67; Chen et al., 2010. Vaccine, 28:5093-5099; Amorij et al., 2008, Pharmaceutical Research, 25(6):1256-1273).

Lipopolysaccharide (LPS) is found in the outer membranes of gram-negative bacteria. LPS can induce inflammation and endotoxic shock in many species. In order to produce vaccines against gram-negative bacteria it is often necessary to remove the LPS to reduce unwanted tissue site reactions, fever, inflammation and the risk of shock. Some of the conventional methods to reduce LPS include purification of proteins by ion-exchange chromatography, affinity adsorbents, gel filtration chromatography and ultrafiltration (Magalhães et al., 2007, J. Pharmacy Pharmaceutical Sci., 10(3):388-404). The choice of purification method is dependent on the biochemical properties of the antigen and the LPS.

In addition to purification and preservation concerns, the proteins used as vaccines are often weakly antigenic and require adjuvants to stimulate a protective immune response in the host. Examples of common adjuvants include aluminum hydroxide, mineral oil emulsions, Freund's adjuvant, virus-like particles, QS-21 and MF59 (Vaccine Adjuvants, Edited by O'Hagan, D., 2000, Humana Press).

SUMMARY OF THE APPLICATION

Provided herein is an insoluble particle that includes polypeptides, wherein the immunogenicity of the polypeptides present in the particles is greater than the immunogenicity of the same polypeptides when they are not present in the particle, and wherein the particle is insoluble. The particle may have a size of 0.1 micrometer to 100 micrometers. The polypeptides may include a microbial outer membrane polypeptide, a microbial porin polypeptide, or a combination thereof. A microbial outer membrane polypeptide or microbial porin polypeptide may be obtained from a member of the family Enterobacteriaceae, family Vibrionaceae, family Pasteurellaceae, or family Pseudomonadaceae. The microbial outer membrane polypeptide may be a metal acquisition polypeptide. In one embodiment, the metal acquisition polypeptide is an iron acquisition polypeptide The iron acquisition polypeptide may have a molecular weight of between 60 kDa and 100 kDa as determined by sodium dodecyl-polyacrylamide gel electrophoresis. The porin polypeptide may have a molecular weight of between 30 kDa and 43 kDa as determined by sodium dodecyl-polyacrylamide gel electrophoresis. The particle may be encapsulated in an implant. The implant may include a biocompatible degradable matrix, such as alginate. The particle may further include an adjuvant. The particle may further include lipopolysaccharide, and the lipopolysaccharide may be insoluble. The particle may further include a carrier, such as zein. In some embodiments, the carrier may be at no greater than 0.001 mg carrier/mg particles.

Also provided herein are compositions. In one embodiment, a composition may include spray dried particles and a pharmaceutically acceptable excipient. The particles may include polypeptides that are soluble before spray drying and insoluble after spray drying, and the particles may include a carrier at a ratio of carrier to polypeptide (weight:weight) of no greater than 0.05:1. The composition may further include a biocompatible degradable matrix, wherein the particles are encapsulated in the biocompatible degradable matrix. An example of a biocompatible degradable matrix includes alginate. The composition may further include an adjuvant. The polypeptides may include a microbial outer membrane polypeptide, a microbial porin polypeptide, or a combination thereof. A microbial outer membrane polypeptide or microbial porin polypeptide may be obtained from a member of the family Enterobacteriaceae, family Vibrionaceae, family Pasteurellaceae, or family Pseudomonadaceae. The microbial outer membrane polypeptide may be a metal acquisition polypeptide. In one embodiment, the metal acquisition polypeptide is an iron acquisition polypeptide. The iron acquisition polypeptide may have a molecular weight of between 60 kDa and 100 kDa as determined by sodium dodecyl-polyacrylamide gel electrophoresis. The porin polypeptide may have a molecular weight of between 30 kDa and 43 kDa as determined by sodium dodecyl-polyacrylamide gel electrophoresis.

Provided herein are methods for preparing a composition. In one embodiment, the method includes spray drying a composition that includes a soluble polypeptide to result in a dry powder, wherein the dry powder is insoluble in an aqueous solution. In one embodiment the composition includes a carrier at a ratio of carrier to polypeptide (weight:weight) of no greater than 0.05:1.

Also provided herein are methods for increasing immunogenicity of a polypeptide. In one embodiment the method includes spray drying a composition that includes a soluble polypeptide to result in a dry powder, wherein the dry powder is insoluble in an aqueous solution, and wherein the particles include a carrier at a ratio of carrier to polypeptide (weight:weight) of no greater than 0.05:1. The method may further include encapsulating the dry powder in a matrix, such as a biocompatible degradable matrix. An example of a biocompatible degradable matrix includes alginate. The composition may further include an adjuvant. The polypeptides may include a microbial outer membrane polypeptide, a microbial porin polypeptide, or a combination thereof. A microbial outer membrane polypeptide or microbial porin polypeptide may be obtained from a member of the family Enterobacteriaceae, family Vibrionaceae, family Pasteurellaceae, or family Pseudomonadaceae. The microbial outer membrane polypeptide may be a metal acquisition polypeptide, in one embodiment, the metal acquisition polypeptide is an iron acquisition polypeptide. The iron acquisition polypeptide may have a molecular weight of between 60 kDa and 100 kDa as determined by sodium dodecyl-polyacrylamide gel electrophoresis. The porin polypeptide may have a molecular weight of between 30 kDa and 43 kDa as determined by sodium dodecyl-polyacrylamide gel electrophoresis.

Further provided herein is a method for inducing the production of antibody in an animal. In one embodiment the method includes administering to an animal an effective amount of a composition. The composition may be one that includes particles, wherein the particles include polypeptides, and wherein the immunogenicity of the polypeptides present in the particles is greater than the immunogenicity of the same polypeptides when they are not present in the particles. The composition may be one that includes spray dried particles and a pharmaceutically acceptable excipient, wherein the particles includes polypeptides that are soluble before spray drying and insoluble after spray drying, and wherein the particles comprise a carrier at a ratio of carrier to polypeptide (weight:weight) of no greater than 0.05:1. The composition may be one that consists essentially of a spray dried insoluble dry powder and lipopolysaccharide, wherein the insoluble dry powder includes polypeptides that are soluble before spray drying, with the proviso that a carrier is not present. The polypeptides may include a microbial outer membrane polypeptide, a microbial porin polypeptide, or a combination thereof. A microbial outer membrane polypeptide or microbial porin polypeptide may be obtained from a member of the family Enterobacteriaceae, family Vibrionaceae, family Pasteurellaceae, or family Pseudomonadaceae. The microbial outer membrane polypeptide may be a metal acquisition polypeptide. In one embodiment, the metal acquisition polypeptide is an iron acquisition polypeptide. The iron acquisition polypeptide may have a molecular weight of between 60 kDa and 100 kDa as determined by sodium dodecyl-polyacrylamide gel electrophoresis. The porin polypeptide may have a molecular weight of between 30 kDa and 43 kDa as determined by sodium dodecyl-polyacrylamide gel electrophoresis.

Also provided herein is a method for decreasing exposure of an animal to lipopolysaccharide. The method includes administering to an animal a composition that includes a spray dried insoluble dry powder, wherein the spray dried insoluble dry powder comprises polypeptides obtained from a gram negative microbe and lipopolysaccharide.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1, 5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Particles

Figure 1:
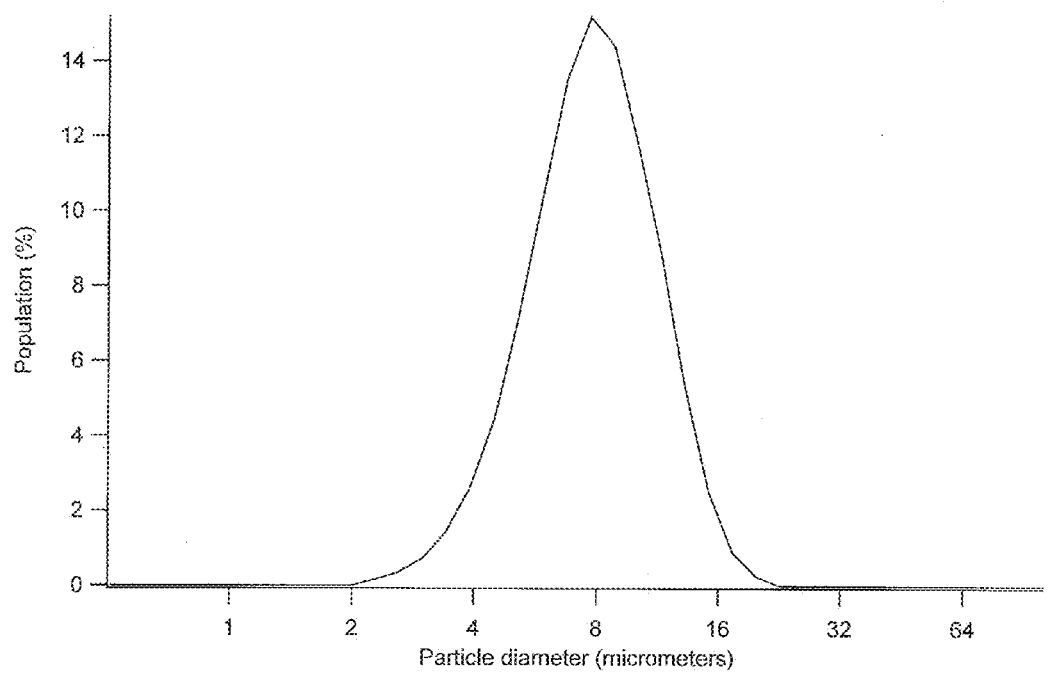
FIG. 1. Particle size distribution of spray dried SRP particles. The distribution plots the percentage of particles in the population with a given diameter.

Provided herein is a particle. A particle may have a diameter of at least 0.1 micrometer, at least 0.5 micrometer, at least 1 micrometer, at least 2 micrometers, at least 3 micrometers, or at least 4 micrometers, and no greater than 100 micrometers, no greater than 70 micrometers, no greater than 40 micrometers, no greater than 20 micrometers, or no greater than 16 micrometers. The average particle size may be 2 micrometers, 4 micrometers, 6 micrometers, 8 micrometers, 10 micrometers, 12 micrometers, 14 micrometers, or 16 micrometers. The particle size may be measured using routine methods such as laser light scattering, which can be conducted using commercially available equipment. As used herein, "powder" refers to a composition that includes a plurality of discrete particles having the characteristics described herein.

A particle may be dry. As used herein, "dry" means that a particle has a moisture and residual solvent content such that the powder is physically and chemically stable in storage at room temperature and is readily dispersible in an aqueous solvent. The moisture and residual solvent content of a particle may be less than 10% by weight, less than 5% by weight, or less than 2% by weight. The moisture and residual solvent content will usually be controlled by the drying conditions, as described in detail below.

In some embodiments a particle is insoluble in an aqueous solution. As used herein, "insoluble" means a particle is insoluble or sparingly or poorly soluble in water. A particle is considered insoluble if no greater than 30% of the weight of the particle dissolves in water at a temperature of 4° C. over 26 hours.

A particle may include at least one type of polypeptide (e.g., all the polypeptides in the particle are the same), or a number of polypeptides that is an integer greater than one (e.g., at least two types, at least three types, at least four types, at least five types, at least six types, at least seven types, at least eight types, at least nine types of polypeptides, etc.). As used herein, the term "polypeptide" refers broadly to a polymer of two or more amino acids joined together by peptide bonds. The term "polypeptide" also includes molecules which contain more than one polypeptide joined by disulfide bonds, ionic bonds, or hydrophobic interactions, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

A polypeptide may be isolated. An "isolated" polypeptide is one that has been removed from its natural environment. For instance, an isolated polypeptide is a polypeptide that has been removed from the cytoplasm or from the membrane of a cell, and many of the polypeptides, nucleic acids, and other cellular material of its natural environment are no longer present. A polypeptide characterized as "isolatable" from a particular source is a polypeptide that, under appropriate conditions, is produced by the identified source, although the polypeptide may be obtained from alternate sources using, for example, recombinant, chemical, or enzymatic techniques well known to those skilled in the art. Thus, characterizing a polypeptide as "isolatable" from a particular source does not imply any specific source from which the polypeptide must be obtained or any particular conditions or processes under which the polypeptide must be obtained. Polypeptides that are produced outside the organism in which they naturally occur, e.g., through chemical or recombinant means, are considered to be isolated, since they were never present in a natural environment.

A polypeptide may be enriched. The term "enriched" defines a specific polypeptide or a specific set of polypeptides constituting a significantly higher fraction (at least 2 fold, at least 5 fold, or at least 10 fold) of the total of polypeptides present in a composition than in the cells from which the polypeptide(s) was separated. A person skilled in the art can preferentially reduce the amount of other polypeptides present, or preferentially increase the amount of specific polypeptides of interest, or both. However, the term "enriched." does not imply that there are no other polypeptides present. Enriched simply means the relative amount of the one or more sequences of interest have been significantly increased. The term also means an increase relative to other polypeptides of at least 2 fold, at least 5 fold, or at least 10 fold. The term also does not imply that there are no amino acid sequences. "Enriched" is meant to include those situations in which a person has intervened to elevate the proportion of the desired polypeptide.

A particle may include a maximum number of different types of polypeptides. In some embodiments, the maximum number of polypeptides can refer to the maximum total number of polypeptides. A particle may include, for example, no more than 50 different types of polypeptides such as, for example, no more than 40, no more than 30, no more than 25, no more than 20, no more than 15, no more than 14, no more than 13, no more than 12, no more than 11, no more than 10, no more than nine, no more than eight, no more than seven, no more than six, no more than five, no more than four, no more than three, no more than two different types of polypeptides, or no more than one type of polypeptide (e.g., all the polypeptides in the particle are the same). In one embodiment, a particle includes at least 0.1 mg polypeptide/mg particles, at least 0.25 mg polypeptide/mg particles, at least 0.5 mg polypeptide/mg particles, at least 0.75 mg polypeptide/mg particles, at least 0.9 mg polypeptide/mg particles, or at least 0.95 mg polypeptide/mg particles.

Polypeptides present in a particle may be from any source. In one embodiment, a particle may include one or more microbial polypeptides. Microbial polypeptides are polypeptides that are expressed by a prokaryotic microbe. Examples of such microbes include, but are not limited to, gram negative microbes and gram positive microbes. Examples of gram negative microbes include, for instance, members of the family Enterobacteriaceae, members of the family Vibrionaceae, members of the family Pseudomonadaceae, members of the family Pasteurellaceae, members of the family Alcaligenaceae, and members of the family Burkholderiaceae.

Examples of members of the family Enterobacteriaceae include, for instance. *E. coli, Shigella* spp., *Salmonella* spp., *Proteus* spp., *Klebsiella* spp. (for instance, *Klebsiella pneumoniae*), *Serratia* spp., and *Yersinia* spp. Examples of *Salmonella* spp. include *Salmonella enterica* serovars, *Bredeney, Dublin, Agona, Blockley, Enteriditis, Typhimurium, Hadar, Heidelberg Montevideo, Muenster, Newport, Senfienberg, Cholerasuis,* and *Typhi*. Examples of strains of *E. coli* include, for example, *E. coli* serotypes O1a, O2a, O78, and O157, different O:H serotypes including 0104, 0111, 026, 0113, 091, *E. coli* O157:H7, and hemolytic strains of enterotoxigenic *E. coli* such as K88$^+$, F4$^+$, F18ab$^+$, and F18ac$^+$, Examples of *Yersinia* spp. include, for instance, *Y. enterocolitica, Y. pestis, and Y. ruckeri*. An example of a member of the family Vibrionaceae includes, for instance, *Vibrio cholerae*. An example of a member of the family Pseudomonadaceae includes, for instance, *Pseudomonas* spp., such as *P. aeruginosa*. An example of a member of the family Pasteurellaceae includes, for instance, *Pasturella* spp., such as *P. multocida* and *P. haemolytica*. Examples of members of the family Alcaligenaceae include, but are not limited to, *Bordetella* spp, such as *B. pertussis, B. parapertussis, B. bronchiseptica*, and *B. avium*. Examples of members of the family Burkholderiaceae include, but are not limited to, *Burkholderia mallei, B. pseudomallei,* and *B. thilandensis*. Other gram negative microbes include *Actinobacillus* spp., *Haemophilus* spp., *Myxcobacteria* spp., *Sporocytophaga* spp., *Chondrococcus* spp., *Cytophaga* spp., *Flexihacter* spp., *Flavobacterium* spp., *Aeromonas* spp., *Campylobacter* spp., *Legionella* spp., *Bruce* spp., *Bordtella* spp., *Helicobacter* spp., and *Neisseria* spp., among other gram-negative bacteria.

Gram positive microbes from which polypeptides may be obtained include members of the family Micrococcaceae, preferably, *Staphylococcus* spp., more preferably, *Staphylococcus aureus*. Other gram positive microbes include members of the family Streptococcaceae, preferably, *Streptococcus agalactiae, Streptococcus uberis, Streptococcus bovis, Streptococcus equi, Streptococcus pyogenes, Streptococcus zooepidemicus*, or *Streptococcus dysgalatiae*. Other gram positive microbes from which polypeptides can be isolated include *Bacillus* spp., *Clostridium* spp., *Corynebacterium* spp., *Erysipelothrix* spp., *Listeria* spp., *Mycobacterium* spp., *Erysipelothrix* spp, *Bacillus* spp., and *Clostridium* spp.

A microbial polypeptide may be one that is normally present in the cytoplasm, the periplasmic space, the inner membrane, or when the microbe is a gram negative, the outer membrane of a microbe. Examples of outer membrane polypeptides include, but are not limited to, metal acquisition polypeptides. A metal acquisition polypeptide allows a microbe to acquire a metal, such as iron, from a host. In one embodiment, an iron acquisition polypeptide allows a microbe to acquire iron from hemoglobin and/or transferrin. One example of such an iron acquisition polypeptide is transferrin binding protein. In another embodiment, an iron acquisition polypeptide allows a microbe to acquire iron from a host by binding a siderophore. Such an iron acquisition polypeptide is a siderophore receptor. Siderophore receptors are known in the art, have been cloned and characterized, and have been the subject of biochemical and molecular biological analysis (Emery et al., U.S. Pat. No. 5,830,479, U.S. Pat. No. 7,138,124, US Patent Application Publication 2005/0186217; Herron-Olson, WO 2010/111273; Crosa, Microbiol. Rev., 1989, 53:517-530; Courcol et al., Infect. Immun., 1997, 65:1944-1948). Examples of siderophore receptors useful herein include, but are not limited to, those reactive with the siderophore aerobactin (molecular weight 72-74 kDa, produced by members of the family Enterobacteriaceae, for example, *E. coli, Salmonella*, and *Klebsiella*, and member of the family Pseudomonadaceae), the siderophore multocidin (molecular weight 500-1000 kDa, produced by members of the family Pasteurellaceae, such as *Pasteurella multocida*), the siderophore enterochelin (molecular weight 81-84 kDa, produced by *E. coli, Salmonella, Pseudomonas*, and *Klebsiella*), the siderophore ferrichrome (molecular weight 78 kDa, produced by *E. coli*, and *Salmonella* spp), and the siderophore coprogen (molecular weight 74-76 kDa, produced by *E. coli*) (Emery et al., U.S. Pat. No. 6,432,412). Siderophore receptors may also be referred to as ChuA (also known as ShuA), Hma, IhaA, IreA, IroN, IutA, FyuA, FepA, FecA, FhuA, BtuB, CirA, FhuE, Fiu, c0294, and c2482. Examples of these polypeptides are well known in the art, and readily available. With the exception of multocidin, the molecular weights of siderophore receptors, as determined by separation of the SRPs using a 12% sodium dodecyl-polyacrylamide gel electrophoresis (SDS-PAGE) gel under reducing and denaturing conditions, are between 60 kDa (kiloDaltons) and 100 kDa, more preferably, between 65 kDa and 95 kDa.

Another example of outer membrane polypeptides include porins. Porins are polypeptides that produce pores or channels allowing passage of molecules across the outer membrane of gram negative microbes (see, for instance, Nikaido and Vaara, Outer Membrane, In: *Escherichia coli* and *Salmonella typhimurium*, Cellular and Molecular Biology, Neidhardt et al., (eds.) American Society for Microbiology, Washington, D.C., pp. 7-22 (1987)) and the membrane of gram positive microbes. For instance, it is believed that the porins produced by gram negative microbes may include OmpA, OmpC, OmpD, OmpF, or PhoE. The porins are relatively conserved between grain negative bacteria, and play a role in iron binding. For example, OmpF and OmpC will bind lactoferrin (Erdei et al., *Infec. Immun.*, 62, 1236-1240 (1994)), while OmpA will bind ferrichrome (Coulton et al., *J. Gen. Microbial*, 110, 211-220 (1979)). Preferably, the molecular weights of porins of the compositions described herein, as determined by separation of the porins using a 12% SDS-PAGE gel under reducing and denaturing conditions, are between 30 kDa and 43 kDa, more preferably, between 33 kDa and 40 kDa. Preferably, the porins are obtained from a gram negative microbe. Typically, different species of *Salmonella* each produce at least two porins. Preferably, when the composition includes porins from a *Salmonella*, the porins are isolated from one species of *Salmonella*. Preferably, the molecular weights of porins isolated from *Salmonella* spp. are between 37 kDa to 40 kDa, more preferably, between 38 kDa and 39 kDa. Typically, *E. coli* produces at least two porins. Preferably, the molecular weights of porins isolated from *E. coli* are between 33 kDa to 39 kDa, more preferably, between 34 kDa and 38 kDa.

Microbial polypeptides useful herein may be iron regulated polypeptides. As used herein, an "iron regulated polypeptide" is a polypeptide that is expressed by a microbe at a greater level when the microbe is grown in low iron conditions compared to growth of the same microbe in high iron conditions. Low iron and high iron conditions are described herein. For instance, an iron regulated polypeptide is not expressed at detectable levels during growth of the microbe in high iron conditions but is expressed at detectable levels during growth in low iron conditions. Examples of iron regulated polypeptides include, but are not limited to, siderophore receptors. Another type of iron regulated polypeptide is expressed at detectable levels during growth of the microbe in high iron conditions but expressed at higher levels during growth in low iron conditions. The expression of such polypeptides is referred to herein as "enhanced" during growth in low iron conditions. In general, iron regulated polypeptides typically have a molecular weight of 66 kDa or greater. Polypeptides expressed that are not iron regulated are typically expressed at about the same level when the microbe is grown in low iron and high iron conditions.

Polypeptides in a particle described herein may have immunogenic activity. "Immunogenic activity" refers to the ability of a polypeptide to elicit an immunological response in an animal. An immunological response to a polypeptide is the development in an animal of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells, directed to an epitope or epitopes of the polypeptide. "Epitope" refers to the site on an antigen to which specific B cells and/or T cells respond so that antibody is produced. The immunogenic activity may be protective. "Protective immunogenic activity" refers to the ability of a polypeptide to elicit an immunological response in an animal that prevents or inhibits infection by *Salmonella* spp., for instance, *S. enterica* serovars, such as *S. enterica* serovar *Newport* and *S. enterica* serovar *Enteritidis* Whether a polypeptide has protective immunogenic activity can be determined by methods known in the art. For example, a polypeptide in a particle described herein, or combination of polypeptides in a particle described herein, protect an avian species such as a turkey against challenge with a *Salmonella* spp. A polypeptide in a particle may have seroreactive activity. "Seroreactive activity" refers to the ability of a candidate polypeptide to react with antibody present in convalescent serum from an animal infected with a

*Salmonella* spp., preferably *S. enterica* serovars, such as *S. enterica* serovar *Newport* or *S. enterica* serovar *Enteritidis*. Polypeptides in a particle may have immunoregulatory activity. "Immunoregulatory activity" refers to the ability of a polypeptide to act in a nonspecific manner to enhance an immune response to a particular antigen. Methods for determining whether a polypeptide has immunoregulatory activity are known in the art.

Optionally, a polypeptide present in a particle can be covalently bound or conjugated to a polypeptide immunogen to improve the immunological properties of the polypeptide. Useful polypeptide immunogens are known in the art. The chemical coupling of polypeptides to polypeptide immunogens can be carried out using known and routine methods. For instance, various homobifunctional and/or heterobifunctional cross-linker reagents such as bis(sulfosuccinimidyl) suberate, bis(diazobenzidine), dimethyl adipimidate, dimethyl pimelimidate, dimethyl superimidate, disuccinimidyl suberate, glutaraldehyde, m-maleimidobenzoyl-N-hydroxysuccinimide, sulfo-m-maleimidobenzoyl-N-hydroxysuccinimide, sulfosuccinimidyl 4-(N-maleimidomethyl)cyclohexane-1-carboxylate, sulfosuccinimidyl 4-(p-maleimidophenyl) butyrate and (1-ethyl-3-(dimethyl-aminopropyl) carbodiimide can be used (see, for instance, Harlow and Lane, Antibodies, A Laboratory Manual, generally and Chapter 5, Cold Spring Harbor Laboratory, Cold Spring Harbor, New York, N.Y. (1988)).

In some embodiments a particle described herein may include a carrier. Carriers may be present to stabilize the polypeptides during processing to produce a particle and/or storage. Examples of carriers include, for instance, carbohydrates (e.g., sugars such as mono-, di-, and polysaccharides), surfactants, amphipathic compounds, proteins, polymers, and plasticisers. Examples of carriers include, but are not limited to, trehalose, mannitol, dextran, poloxamers, PVP, leucine, lysin, zein, inositol, gelatin, glycerol, and inulin. In one embodiment, a particle described herein contains no greater than 0.001 mg carrier/mg particles, no greater than 0.005 mg carrier/mg particles, no greater than 0.01 mg carrier/mg particles, no greater than 0.05 mg carrier/mg particles, no greater than 0.1 mg carrier/mg particles, no greater than 0.25 mg carrier/mg particles, no greater than 0.5 mg carrier/mg particles, or no greater than 0.75 mg carrier/mg particles. In one embodiment, a particle does not include a carrier. In one embodiment, a particle includes a carrier at a concentration of at least 0.001 mg carrier/mg particles, at least 0.005 mg carrier/mg particles, at least 0.01 mg carrier/mg particles, at least 0.05 mg carrier/mg particles, at least 0.1 mg carrier/mg particles, at least 0.25 mg carrier/mg particles, at least 0.5 mg carrier/mg particles, or at least 0.75 mg carrier/mg particles. In one embodiment, a carrier is zein, a class of prolamine polypeptide present in corn. Zein is commercially available from, for instance, Freeman Industries (Tuckahoe, N.Y.). In one embodiment, a particle includes a carrier at a ratio of carrier to polypeptide (weight:weight) of no greater than 0.05:1, no greater than 0.08:1, no greater than 0.1:1, no greater than 0.3:1, no greater than 0.5:1, no greater than 1:1, no greater than 2:1, no greater than 4:1, no greater than 6:1, or no greater than 8:1. In one embodiment, a particle includes a carrier at a ratio of carrier to polypeptide (weight:weight) of at least 0.5:1, at least 1:1, at least 5:1, at least 10:1, at least 15:1, at least 20:1, or at least 25:1. In one embodiment, a particle does not include a detectable amount of a carrier. The ability to not use a carrier but maintain activity of the polypeptides was unexpected in view of the recognized use of carriers to reduce shear stress, heating stress, and dehydration stress during production of a particle (Saluja et al., 2010, J Controlled Release, 144:127-133, Ohtake et al., 2010, Vaccine, 28:1275-1284).

The polypeptides used in the preparation of a particle may be in a solution that includes components commonly used in preserving polypeptide structure in an aqueous solution. Examples of such components include, for instance, components for maintaining ionic strength, pH, etc. In some embodiments a particle may include such components, which may be, for instance, a biological buffer such as Tris or other organic compounds that function as a biological buffer. Other components present may include preservatives, such as formalin.

A particle may also include an adjuvant. An "adjuvant" refers to an agent that can act in a nonspecific manner to enhance an immune response to a particular antigen, thus potentially reducing the quantity of antigen and/or the frequency of injection necessary in order to generate an adequate immune response to a polypeptide present in a particle. Adjuvants may include, for example, IL-1, IL-2, emulsifier, muramyl dipeptides, dimethyl dioctadecyl ammonium bromide (DDA), pyridine, hydroxides such as aluminum and magnesium (including, for instance, those available from under the tradename IMJECT ALUM from Thermo Scientific, Rockford, Ill.), oils, saponins, alpha-tocopherol, polysaccharides, emulsified paraffins (including, for instance, those available from under the tradename EMULSIGEN from MVP Laboratories, Ralston, Nebr.), ISA-70, RIBI and other substances known in the art. It is expected that polypeptides in a particle described herein will have immunoregulatory activity and that such polypeptides may be used as adjuvants that directly act as T and/or B cell activators or act on specific cell types that enhance the synthesis of various cytokines or activate intracellular signaling pathways. Such polypeptides are expected to augment the immune response to increase the protective index of the polypeptides present in a particle.

In another embodiment, a particle described herein can include a biological response modifier, such as, for example, IL-2, IL-4 and/or IL-6, TNF, IFN-alpha. IFN-gamma, and other cytokines that effect immune cells.

In some embodiments a particle described herein may include lipopolysaccharide (LPS). LPS is a component of the outer membrane of most gram negative microbes (see, for instance, Nikaido and Vaara, Outer Membrane, In: *Escherichia coli* and *Salmonella typhimurium*, Cellular and Molecular Biology, Neidhardt et al., (eds.) American Society for Microbiology, Washington, D.C., pp. 7-22 (1987), and typically includes polysaccharides (O-specific chain, the outer and inner core) and the lipid A region. In some embodiments LPS present in a particle has limited solubility in an aqueous solution. In some embodiments, LPS is released from the particles at a rate of no greater than 10% EU/ml during the first 26 hours of incubating a sample of 1 gram of particles in 100 mls of water at 4° C. This decreased release of LPS from the particles was unexpected.

The concentration of LPS can be determined using routine methods known in the art. Such methods typically include measurement of dye binding by LPS (see, for instance, Keler and Nowotny, *Analyt. Biochem.,* 156, 189 (1986)) or the use of a *Limulus* amebocyte lysate (LAL) test (see, for instance, Endotoxins and Their Detection With the *Limulus* Amebocyte Lystate Test, Alan R. Liss, Inc., 150 Fifth Avenue, New York, N.Y. (1982)). There are four basic commercially available methods that are typically used with an LAL test: the gel-clot test; the turbidimetric (spectrophotometric) test; the colorimetric test; and the chromogenic test. An example of a gel-clot assay is available under the tradename E-TOXATE (Sigma Chemical Co., St. Louis, Mo.; see Sigma Technical Bulletin No, 210), and PYROTELL (Associates of Cape Cod, Inc., East Falmouth, Mass.). Typically, assay conditions include contacting the composition with a preparation containing a lysate of the circulating amebocytes of the horseshoe crab, Limulus polyphemus. When exposed to US, the lysate increases in opacity as well as viscosity and may gel. About 0.1 milliliter of the composition is added to lysate. Typically, the pH of the composition is between 6 and 8, preferably, between 6.8 and 7.5. The mixture of composition and lysate is incubated for about 1 hour undisturbed at about 37° C. After incubation, the mixture is observed to determine if there was gelation of the mixture. Gelation indicates the presence of endotoxin. To determine the amount of endotoxin present in the composition, dilutions of a standardized solution of endotoxin are made and tested at the same time that the composition is tested. Standardized solutions of endotoxin are commercially available from, for instance, Sigma Chemical (Catalog No. 210-SE), U.S. Pharmacopeia (Rockville, Md., Catalog No. 235503), and Associates of Cape Cod, Inc., (Catalog No. E0005).

A particle may include polypeptides isolatable from one microbe, or isolatable from a combination of two or more microbes. For instance, a composition can include polypeptides isolatable from two or more Salmonella spp., or from a Salmonella spp. and a different microbe that is not a member of the genus Salmonella, such as E. coli.

Polypeptides present in a particle described herein may be obtained from a microbe, or produced using recombinant, chemical or enzymatic synthesis techniques. The methods for obtaining such polypeptides are known and routine. Such methods include those described in, for instance, Emery et al., (U.S. Pat. No. 7,160,549, U.S. Patent Application US 20050186217-A1, 20050095682-A1, 20060083753-A1, and 20060269564-A1). Microbes useful for obtaining polypeptides useful herein are readily available. For instance, microbes are commercially available from a depository such as American Type Culture Collection (ATCC). In addition, such microbes are readily isolatable by techniques routine and known in the art. The microbes may be derived from an infected animal as a field isolate, and used to obtain polypeptides useful herein, or stored for future use, for example, in a frozen repository at −20° C. to −95° C., in bacteriological media containing 20% glycerol, and other like media.

When a particle described herein is to include iron regulated polypeptides obtained from a microbe, the microbe can be incubated under low iron conditions. As used herein, the phrase "low iron conditions" refers to an environment, typically bacteriological media, which contains amounts of free iron that cause a microbe to express or enhance expression of iron regulated polypeptides. As used herein, the phrase "high iron conditions" refers to an environment that contains amounts of free iron that cause a microbe to either not express one or more of an iron regulated polypeptide at a detectable level, or to decrease expression of such a polypeptide.

Low iron conditions are generally the result of the addition of an iron chelating compound to a bacteriological medium, or the use of bacteriological media formulated to contain low amounts of iron. High iron conditions are generally present when a chelator is not present in the medium, iron is added to the medium, or the combination thereof. Examples of metal chelators include natural and synthetic compounds. Examples of natural compounds include plant phenolic compounds, such as flavenoids. Examples of flavenoids include the iron chelators myricetin and quercetin. Examples of synthetic iron chelators include 2,2'-dipyridyl (also referred to in the art as α,α'-bipyridyl), 8-hydroxyquinoline, ethylenediamine-di-O-hydroxyphenylacetic acid (EDDHA), desferrioxamine methanesulphonate (desferol), transferrin, lactoferrin, ovotransferrin, biological siderophores, such as, the catecholates and hydroxamates, and citrate. Preferably, 2,2'-dipyridyl is used for the chelation of iron. When the microbe is a gram negative, 2,2'-dipyridyl may added to the media at a concentration of at least 0.0025 micrograms/milliliter (μg/ml), at least 0.025 μg/ml, or at least 0.25 μg/ml, and generally no greater than 10 μg/ml, no greater than 20 μg/ml, or no greater than 30 μg/ml. When the microbe is a gram positive, such a Staphylococcus aureus, 2,2'-dipyridyl may added to the media at a concentration of at least 300 μg/ml, at least 600 μg/ml, or at least 900 μg/ml. High levels of 2,2'-dipyridyl can be 1200 μg/ml, 1500 μg/ml, or 1800 μg/ml.

The medium used to incubate the microbe and the volume of media used to incubate the microbe can vary. When a microbe is being evaluated for the ability to produce one or more of the polypeptides useful herein, the microbe can be grown in a suitable volume, for instance, 10 milliliters to 1 liter of medium. When a microbe is being grown to obtain polypeptides for use in, for instance, the production of particles for administration to animals, the microbe may be grown in a fermentor to allow the isolation of larger amounts of polypeptides. Methods for growing microbes in a fermentor are routine and known in the art. The conditions used for growing a microbe preferably include an iron chelator, for instance 2,2'-dipyridyl, a pH of between 6.5 and 7.5, preferably between 6.9 and 7.1, and a temperature of 37° C.

A microbe may be harvested after growth. Harvesting includes concentrating the microbe into a smaller volume and suspending in a media different than the growth media. Methods for concentrating a microbe are routine and known in the art, and include, for example, filtration or centrifugation. Typically, the concentrated microbe is suspended in decreasing amounts of buffer. Preferably, the final buffer includes a cation chelator, preferably, ethylenediaminetetraacetic acid (EDTA). An example of a buffer that can be used contains Tris-base (7.3 grams/liter) and EDTA (0.9 grams/liter), at a pH of 8.5. Optionally, the final buffer also minimizes proteolytic degradation. This can be accomplished by having the final buffer at a pH of greater than 8.0, preferably, at least 8.5, and/or including one or more proteinase inhibitors (e.g., phenylmethanesulfonyl fluoride). Optionally and preferably, the concentrated microbe is frozen at −20° C. or below until disrupted.

The microbe may be disrupted using chemical, physical, or mechanical methods routine and known in the art, including, for example, french press, sonication, or homogenization. Preferably, homogenization is used. An example of a suitable device useful for homogenization is a model C500 Avestin Homogenizer, (Avestin Inc, Ottawa Canada). As used herein, "disruption" refers to the breaking up of the cell. Disruption of a microbe can be measured by methods that are routine and known in the art, including, for instance, changes in optical density. Typically, a microbe is subjected to disruption until the percent transmittance is increased by 20% when a 1:100 dilution is measured. The temperature during disruption is typically kept low, preferably at 4° C., to further minimize proteolytic degradation.

The disrupted microbe is solubilized in a detergent, for instance, an anionic, zwitterionic, nonionic, or cationic detergent. Preferably, the detergent is sarcosine, more preferably, sodium lauroyl sarcosinate. As used herein, the term "solubilize" refers to dissolving cellular materials (e.g., polypeptides, nucleic acids, carbohydrates) into the aqueous phase of the buffer in which the microbe was disrupted, and the formation of aggregates of cellular materials. The conditions for solubilization preferably result in the aggregation of polypeptides useful herein into aggregates that are large enough to allow easy isolation by, for instance, centrifugation.

Significant decreases in LPS are typically observed when the disrupted microbe is solubilized in higher levels of sarcosine, solubilized for longer periods, or the combination thereof. Preferably, the sarcosine is added such that the final ratio of sarcosine to gram weight of disrupted microbe is between 1.0 gram sarcosine per 4.5 grams pellet mass and 6.0 grams sarcosine per 4.5 grams pellet mass, preferably, 4.5 gram sarcosine per 4.5 grams pellet mass. The solubilization of the microbe may be measured by methods that are routine and known in the art, including, for instance, changes in optical density. Typically the solubilization is allowed to occur for at least 24 hours, preferably, at least 48 hours, more preferably, at least 72 hours, most preferably, at least 96 hours. The temperature during disruption is typically kept low, preferably at 4° C.

The aggregates that include one or more polypeptides, for instance, iron regulated polypeptides, useful herein may be isolated by methods that are routine and known in the art. Preferably, the aggregates are isolated by centrifugation. Typically, centrifugation of the aggregates requires centrifugal forces of at least 50,000×g, typically 100,000×g. The use of such centrifugal forces requires the use of ultracentrifuges, and scale-up to process large volumes of sample is often difficult and not economical with these types of centrifuges. The methods described herein provide for the production of aggregates large enough to allow the use of significantly lower centrifugal forces (for instance, 46,000×g). Methods for processing large volumes at these lower centrifugal forces are available and known in the art. Thus, the aggregates can be isolated at a significantly lower cost. Examples of suitable devices useful for centrifugation of large volumes include T-1. Sharpies, (Alfa Laval Separations, Warminster, Pa.) and Hitachi Himac CC40 high speed centrifuges (Hitachi-Koki Co, Tokyo, Japan).

Optionally and preferably, the sarcosine is removed from the isolated polypeptides. Methods for removing sarcosine from the isolated polypeptides are known in the art, and include, for instance, diafiltration, precipitation, hydrophobic chromatography, ion exchange chromatography, or affinity chromatography, and ultra filtration and washing the polypeptides in alcohol by diafiltration. After isolation, the polypeptides were suspended in buffer and stored at low temperature, for instance, −20° C. or below.

Polypeptides useful herein may also be isolated from microbes using methods that are known to the art. The isolation of the polypeptides may be accomplished as described in, for instance, Emery et al., (U.S. Pat. No. 5,830,479, U.S. Pat. No. 7,138,124, US Patent Application 2005/0186217) and Herron-Olson, WO 2010/111273.

Compositions

Provided herein are compositions that include a particle. A composition will usually include a plurality of parades. A composition can include a single type of particle (e.g., each particle in the composition includes the same polypeptide), or a mixture of particles (e.g., the composition includes at least 2 different populations of particles).

A composition described herein optionally further includes a pharmaceutically acceptable excipient. "Pharmaceutically acceptable" refers to a pharmacologically inactive substance that is compatible with the other ingredients of the composition, and not deleterious to the recipient thereof. Typically, the composition includes a pharmaceutically acceptable excipient when the composition is used as described herein. The compositions may be formulated in pharmaceutical preparations in a variety of forms adapted to the chosen route of administration, including routes suitable for stimulating an immune response to an antigen. Thus, a composition can be administered via known routes including, for example, oral; parenteral including intradermal, transcutaneous and subcutaneous; intramuscular, intravenous, intraperitoneal, etc. and topically, such as, intranasal, intrapulmonary, intramammary, intravaginal, intrauterine, intradermal, transcutaneous and rectally, etc. It is foreseen that a composition can be administered to a mucosal surface, such as by administration to the nasal or respiratory mucosa (e.g., via a spray or aerosol), in order to stimulate mucosal immunity, such as production of secretory IgA antibodies, throughout the animal's body.

A composition described herein can also be administered via an implant which contains particles described herein. Implants include known implant matrices suitable for administration in living tissues. Typically, the implant matrix, includes a biocompatible, non-toxic material that allows for incorporation of a particle and subsequent release of the particle and/or polypeptides contained in the particle. An implant may or may not be biodegradable, bioerodible or bioabsorbable.

The term "biocompatible" means that the implant matrix does not cause substantial tissue irritation or necrosis at the implant site. The term "biodegradable" means that the implant matrix degrades over time by enzymatic or hydrolytic action, or other mechanism in the animal's body. The term "bioerodible," means that the implant erodes or degrades over time by contact with surrounding tissue fluids, through cellular activity or other physiological degradation mechanisms. By "bioabsorbable," it is meant that the implant matrix breaks down and is absorbed by a cell, tissue, or other mechanism within the animal's body.

The particle and/or polypeptides contained in the particle can be released from the implant as a sustained release, delayed release or a combination thereof. Preferably, the amount of particles and/or polypeptides contained in the particles that is released is effective to induce a primary immune response to the polypeptides.

A preferred implant can be made from a biocompatible solid phase polymeric, matrix that allows for structural integrity and is bioabsorbable, biodegradable, and/or bioerodible in the body of an animal and will not cause irritation or an adverse effect to the animal. The implant can be administered as a single unit or multiples thereof, each may have the same release kinetics or a combination of different release times.

A sustained release implant provides release of particles and/or polypeptides contained in the particles in a substantially continuous manner. Sustained release of particles and/or polypeptides contained in the particle from an implant can begin immediately at administration up to 48 hours after administration, typically 24 hours depending on the composition of the implant matrix. Various known coatings, including polymer coatings, can also be applied to the implant to affect the time at which the sustained release of the particle and/or polypeptides begins. Examples of suitable sustained release implant matrices include polymeric matrix delivery systems such as disclosed in Folkman et al. (U.S. Pat. No. 4,164,560) and cholesterol matrix delivery systems such as disclosed in Kent (U.S. Pat. No. 4,452,775). Other matrices include cellulosic polymers, copolymers of D-mannuronic acid and L-guluronic acid, polylactide, polycaprolactone, polyglycolides, etc.

A delayed release implant matrix can provide a "pulse" or "burst" of particle and/or polypeptide release from the implant at a predetermined time post administration. Different matrices provide release at different times.

In one embodiment a combination of a sustained release and a delayed release matrix can be used. Such implants could provide for early release of particles and/or polypeptides to stimulate an immune response in an animal, followed by a burst of antigen at a later time to serve as, for instance, a booster for maximizing the efficacy of the immunization.

An implant matrix may include a core containing the particles and an outer coating. Both the core and coating compositions can affect timing and rate of particle release. The core can include lactose, fibrin, methylcellulose, collagen, cholesterol, carbowax, dibutylphthalate (DBP) polyvinyl pyrrolidene (PVP), zinc or magnesium stearate, stearic acid, polyethylene glycol (PEG), silica, etc. Examples of preferred materials include D, lactide, polyacetal polymers, polyorthoesters, polyesteramides, polycaprolactone, polycarbonates, polyhydroxy buterate, polymaleamides, etc.

The outer coating can be a polymer. Examples of useful polymers for forming an outer coating that is biodegradable and bioabsorbable include polycationic polymers, including, for example, polylysine, polyornithine, polyethyleneimine and polylactides, polyglycolides, polycaprolactones, polyanhydrides, polyamides, or copolymers thereof such as copolymers of polyamides and polyesters, copolymers of PLA and PGA, etc. In general, the in vivo life of an implant formulated with such polymers will depend at least in part, on the molecular weight and degree of crosslinking of the polymer in the matrix. Formulations for such matrices are known in the art, as disclosed for example, in Yolles (U.S. Pat. No. 3,887,699) and Huchinson (U.S. Pat. No. 4,767,628). Another useful biodegradable implant material for a syringeable, in-situ forming solid implant made of a thermoplastic or thermosetting polymer system is described in Dunn et al. (U.S. Pat. Nos. 4,938,763 and 5,324,519).

The implant can be formulated to provide delayed and sustained release of a particle. According to one embodiment, timing and rate of release can be a result of the matrix used. A single administration providing sustained and delayed release can include a mixture of implants having different release rates. By varying the matrix, the particle can provide sustained release for an initial period of time by the first biodegradable implant. A second set of implants, providing delayed release can then begin to release as the first implant begins to decline.

Other implants useful in the method include biodegradable, metabolizable, cholesterol-based pellets that provide for slow release of particles. Cholesterol-based implants have been described for slow release of biotin and other micronutrients, and proteins, polynucleotides, polysaccharides, for example, Kent (U.S. Pat. No. 4,452,775) and Wolfrom (U.S. Pat. No. 4,326,523). Also useful are implants having a peptide/polymer matrix, for example, tyrosine dipeptides and polymers as described in Kohn (U.S. Pat. No. 4,863,735), and Kohn et al., (1986, J. Immunol. Methods 95:31-38), that will degrade to form a product having adjuvant activity for the antigen or other bioactive compound incorporated into the matrix.

The matrix may optionally be formulated to include a soluble or insoluble pore-forming agent that will dissipate from the matrix into surrounding tissue fluids causing the formation of pores and/or channels throughout the implant matrix. Examples of such pore-forming agents include sodium chloride, calcium carbonate, calcium phosphate and other salts; carboxymethylcellulose, polyethylene glycol, sodium alginate, agarose and other polymers; starch, glucose and other carbohydrates; amino acids and low molecular weight non-immunogenic proteins etc.

A composition described herein may be administered in an amount sufficient to treat certain conditions as described herein. The amount of particles present in a composition can vary. In one embodiment, the dosage may be based on the amount of polypeptide delivered. For instance, the dosage of polypeptides may be between 0.01 mg and 300 mg, such as between 0.1 mg and 0.25 mg. For an injectable composition (e.g. subcutaneous, intramuscular, etc.) the polypeptides may be present in the composition in an amount such that the total volume of the composition administered is 0.1 ml to 5.0 nil, for instance, 0.1 ml, 0.2 ml, 0.3 ml, 0.4 ml, 0.5 ml, 1.0 ml, 2.0 ml, 3.0 ml, 4.0 ml, or 5.0 ml. The amount administered will vary depending on various factors including, but not limited to, the specific polypeptides chosen, the weight, physical condition and age of the animal, and the route of administration. Thus, the absolute weight of the polypeptide included in a given unit dosage form can vary widely, and depends upon factors such as the species, age, weight and physical condition of the animal, as well as the method of administration. Such factors can be determined by one of skill in the art.

The formulations may be conveniently presented in unit dosage form and may be prepared by methods well known in the art of pharmacy. Methods of preparing a composition with a pharmaceutically acceptable excipient include the step of bringing the active compound (e.g., a polypeptide or whole cell) into association with one or more accessory ingredients. In general, the formulations are prepared by uniformly and intimately bringing the active compound into association with a liquid accessory ingredient, a finely divided solid accessory ingredient, or both, and then, if necessary, shaping the product into the desired formulations.

A composition including a pharmaceutically acceptable excipient can also include an adjuvant. Such an adjuvant may be in addition to any adjuvant which may be incorporated in the particle. The adjuvant which is in a composition, not including any adjuvant which may be incorporated in the particle, may be at a level between 5% and 30% of the volume of the composition, such as between 15% and 25%. In another embodiment, a composition including a pharmaceutically acceptable excipient can include a biological response modifier.

Methods of Making Particles

A particle of the present composition may be prepared by spray-drying. Spray-drying may be carried out, for example, as described generally in the "Spray-drying Handbook", 5$^{th}$ ed., K. masters, John Wiley &: Sons, Inc., New York, N.Y., 1991, and in Platz, R., et al. (WO 97/41833 and WO 96/32149), Cal and Sollohub, 2010, J. Pharma. Sci., 99:575-586, and Sollohub and Cal, 2010, J. Pharma. Sci., 99:587-597).

To prepare polypeptides for spray-drying, polypeptides may be dissolved or suspended in a liquid to form a mixture. A mixture may include polypeptides at a concentration between at least 1 mg/ml and no greater than 50 mg/ml. Preferred examples of concentrations of polypeptides include, for instance, 6 mg/ml, 8 mg/ml, 10 mg/ml, 12 mg/ml, 15 mg/ml, and 20 mg/ml.

The liquid may be an aqueous solvent e.g., water) or an organic solvent. In some embodiments, polypeptides may be spray-dried using an organic solvent or co-solvent system, employing one or more solvents such as acetone, alcohols (e.g., methanol and ethanol), ethers, aldehydes, hydrocarbons, ketones and polar aprotic solvents. Mixtures of aqueous and organic solvents may be used. In one embodiment, a mixture of ethanol and water, such as 70% and 30%, respectively, may be used. The liquid may optionally contain other components in addition to polypeptides, such as, for instance, a carrier to stabilize the polypeptides during processing and/or storage. A carrier may be present in the mixture at a level as described herein, including a concentration that leads to glass formation (see, for instance, Amorij et al., 2008, Pharma. Res., 25:1256-1273). In other embodiments, the mixture does not contain, a carrier. The liquid may also include other components such as components commonly used in stabilizing polypeptides in solution, an adjuvant, a biological response modifier, and/or LPS. In some embodiments, the amount of adjuvant included may be a function of the amount of polypeptide in the mixture. For example, the amount of adjuvant in the mixture may be between 0.1% and 10% (wt/wt) with respect to the amount of polypeptide in the mixture, for instance, between 2% and 7%. The pH range of the mixture is generally between 7.0 and 7.4.

The polypeptide containing solutions are then spray dried in a conventional spray drier, such as those available from commercial suppliers such as Niro A/S (Denmark), Büchi (Switzerland) and the like, resulting in particles described herein. Optimal conditions for spray-drying the polypeptides will vary depending upon the polypeptides used and the presence of any other components such as adjuvants, and are generally determined experimentally. The gas used to spray-dry the material is typically an air/nitrogen mixture, although mixtures including other inert gases such as argon are suitable, as is the use of just air or an inert gas. The optimal temperature of the gas used to dry the sprayed material may be determined experimentally, although generally, the temperature will range from 110° C. to 130° C. Spray drying is often used to increase the solubility of compounds. The significant decrease in solubility of polypeptides, such as outer membrane polypeptides, after spray drying was unexpected.

Alternatively, a particle described herein may be prepared by lyophilization, vacuum drying, spray freeze drying, super critical fluid processing, air drying, or other forms of evaporative drying.

The particles may be maintained under dry (i.e., relatively low humidity) conditions during manufacture, processing, and storage.

Methods of Use

Also provided herein are methods of using the compositions described herein. The methods include administering to an animal an effective amount of a composition described herein. The animal can be, for instance, avian (including, for instance, chickens or turkeys), bovine (including, for instance, cattle), caprine (including, for instance, goats), ovine (including, for instance, sheep), porcine (including, for instance, swine), bison (including, for instance, buffalo), equine (including, for instance, horses), a companion animal (including, for instance, dogs or cats), members of the family Cervidae (including, for instance, deer, elk, moose, caribou and reindeer), or human. The animal may be an embryo (e.g., in ovo or in utero), recently born (e.g., 1 day old, 2 days old, 3 days old, 1 week old, 2 weeks old, 3 weeks old, 4 weeks old, 5 weeks old, 6 weeks old, etc.), an adolescent, or an adult. In one embodiment, an animal may be 1 month old, 3 months old, 5 months old, 7 months old, 9 months old, 11 months old, or 12 months old.

In some aspects, the methods may further include additional administrations (e.g., one or more booster administrations) of the composition to the animal to enhance or stimulate a secondary immune response. A booster can be administered at a time after the first administration, for instance, one to eight weeks, such as two to four weeks, after the first administration of the composition. Subsequent boosters can be administered one, two, three, four, or more times annually. Without intending to be limited by theory, it is expected that in some aspects animal boosters will not be necessary, as an animal will be challenged in the field by exposure to microbes expressing polypeptides present in the compositions having epitopes that are identical to or structurally related to epitopes present on polypeptides of the composition administered to the animal.

In one aspect, provided herein are methods for making antibodies, for instance by inducing the production of antibody in an animal, or by recombinant techniques. Thus, the method includes administering an effective amount of the composition described herein to an animal. The antibody produced includes antibody that specifically binds at least one polypeptide present in the composition. Methods for determining whether an animal has produced antibodies that specifically bind polypeptides present in a composition can be determined using routine methods.

In one embodiment, the animal may have circulating maternal antibody that binds to a polypeptide present in the administered composition. In one embodiment, the animal may be immuno-incompetent. As used herein, "immuno-incompetent" means an animal is incapable of mounting an active immune response to a polypeptide present in the administered composition. The presence of maternal antibody and immuno-incompetence are not mutually exclusive, and in fact circulating maternal antibody can cause an animal to be immuno-incompetent by inhibiting the ability of an animal to mount an immune response to an antigen. Accordingly, in one embodiment the method includes administering to an animal a composition described herein where the particle is present in an implant. The implant may be designed for sustained release of polypeptide for a time such that antigen continues to be released after circulating maternal antibody disappears from the animal and the animal is able to mount an immune response. The administration to a young animal of an implant that maintains release of polypeptide long enough to result in an immune response when maternal antibody is depleted and the animal is immunocompetent is an advantage. The ability to use a single administration reduces handling, decreases the stress young animals encounter, and decreases costs associated with animal husbandry. In one embodiment, the implant includes alginate. An implant made of alginate is generally not useful for extended release of polypeptide because the polypeptide quickly diffuses out of the matrix. However, by using particles that contain polypeptides, the release of polypeptides is slowed considerably and presents an economical method for sustained polypeptide release when compared to other more expensive matrices. The method may be used to produce antibody that specifically binds polypeptides expressed by a microbe other than the microbe from which the polypeptides of the composition were isolated. As used herein, an antibody that can "specifically bind" a polypeptide is an antibody that interacts with the epitope of the antigen that induced the synthesis of the antibody, or interacts with a structurally related epitope. At least some of the polypeptides that may be present in the compositions typically include epitopes that are conserved in the polypeptides of different species and different genera of microbes. Accordingly, antibody produced using a composition that includes polypeptides derived from one microbe is expected to bind to polypeptides expressed by other microbes and provide broad spectrum protection against microbes. For instance, when the polypeptides in a composition are polypeptides expressed by a gram negative microbe such as a *Salmonella* spp., examples of gram negative microbes to which the antibody may specifically bind include members of the family Enterobacteriaceae, members of the family Vibrionaceae, members of the family Pseudomonadaceae, members of the family Pasteurellaceae, and/or other gram negative microbes. When the polypeptides in a composition are polypeptides expressed by a gram positive microbe such as a *Staphylococcus* spp., examples of gram positive microbes to which the antibody may specifically bind are members of the family Micrococcaceae, members of the family Streptococcaceae, and/or other gram positive microbes.

In one aspect, methods provided herein are also directed to treating an infection in an animal caused by a microbe. The microbe causing the infection may be a gram negative microbe, such as a member of the family Enterobacteriaceae, a member of the family Vibrionaceae, a member of the family Pseudomonadaceae, a member of the family Pasteurellaceae, and/or another gram negative microbes. In one embodiment the gram negative microbe may be *Salmonella* spp., such as *S. enterica* serovars, such as *S. enterica* serovar *Newport* or *S. enteritica* serovar *Enteritidis*. The microbe causing the infection may be a gram positive microbe, such as a member of the family Micrococcaceae, a member of the family Streptococcaceae, and/or another gram positive microbe. As used herein, the term "infection" refers to the presence of a microbe in an animal's body, which may or may not be clinically apparent. An animal with an infection by a microbe that is not clinically apparent is often referred to as an asymptomatic carrier.

Treating an infection can be prophylactic or, alternatively, can be initiated after the animal is infected by the microbe. Treatment that is prophylactic—e.g., initiated before a subject is infected by a microbe or while any infection remains subclinical—is referred to herein as treatment of a subject that is "at risk" of infection. As used herein, the term "at risk" refers to an animal that may or may not actually possess the described risk. Thus, typically, an animal "at risk" of infection by a microbe is an animal present in an area where animals have been identified as infected by the microbe and/or is likely to be exposed to the microbe even if the animal has not yet manifested any detectable indication of infection by the microbe and regardless of whether the animal may harbor a subclinical amount of the microbe. Accordingly, administration of a composition can be performed before, during, or after the animal has first contact with the microbe. Treatment initiated after the animal's first contact with the microbe may result in decreasing the severity of symptoms and/or clinical signs of infection by the microbe, completely removing the microbe, and/or decreasing the likelihood of experiencing a clinically evident infection compared to an animal to which the composition is not administered. The method includes administering an effective amount of the composition described herein to an animal having, or at risk of having, an infection caused by a microbe, and optionally determining whether the number of microbes causing the infection has decreased. Methods for determining whether an infection is caused by a microbe are routine and known in the art, as are methods for determining whether the infection has decreased.

In another aspect, the methods are provided for treating one or more symptoms or clinical signs of certain conditions in an animal that may be caused by infection by a microbe, such as a gram negative microbe or a grant positive microbe. The gram negative microbe may be a member of the family Enterobacteriaceae, a member of the family Vibrionaceae, a member of the family Pseudomonadaceae, a member of the family Pasteurellaceae, and/or another gram negative microbe. In one embodiment the gram negative microbe may be *Salmonella* spp., such as *S. enterica* serovar, such as *S. enterica* serovar *Newport* or *S. enterica* serovar *Enteritidis*.

The gram positive microbe may be a member of the family Micrococcaceae, a member of the family Streptococcaceae, and/or another gram positive microbe. The method includes administering an effective amount of a composition described herein to an animal having or at risk of having a condition, or exhibiting symptoms and/or clinical signs of a condition, and optionally determining whether at least one symptom and/or clinical sign of the condition is changed, preferably, reduced. Examples of conditions and/or clinical signs caused by microbial infections include, but are not limited to, mastitis, septicemia, pneumonia, meningoencephalitis, lymphangitis, dermatitis, genital tract infections, strangles, metritis, perinatal disease, pituitary abscesses, arthritis, bursitis, orchitis, cystitis and pyelonephritis, caseous lymphadenitis, tuberculosis, ulcerative lymphangitis, listeriosis, erysipelas, laminitis, anthrax, tyzzer's disease, tetanus, botulism, enteritis, malignant edema, braxy, bacillary hemoglobinuria, enterotoxemia, necrotic skin lesions, and nosocomial infections. Example of conditions caused by *Salmonella* include, for instance, pullorum disease, fowl typhoid and paratyphoid, which is characterized by anorexia, diarrhea, reduced egg production, dehydration, blindness and lameness. Examples of conditions caused by *S. aureus* include, for instance, botryomycosis in horses, purulent synovitis and osteomyelitis in poultry, abortions in swine, and tick pyemia in lambs. Examples of conditions caused by *Streptococcus* spp. include, for instance, sore throat, scarlet fever, impetigo, Ulcerative endocarditis, rheumatic fever and post streptococcal glomerulonephritis cervicitis in humans, cervicitis in equine and swine, and meningitis and jowl abscesses in swine.

Treatment of symptoms and/or clinical signs associated with these conditions can be prophylactic or, alternatively, can be initiated after the development of a condition described herein. As used herein, the term "symptom" refers to subjective evidence of disease or condition experienced by the patient and caused by infection by a microbe. As used herein, the term "clinical sign" or, simply, "sign." refers to objective evidence of disease or condition caused by infection by a microbe. Symptoms and/or clinical signs associated with conditions referred to herein and the evaluations of such symptoms are routine and known in the art. Treatment that is prophylactic, for instance, initiated before a subject manifests symptoms or signs of a condition caused by a microbe, is referred to herein as treatment of a subject that is "at risk" of developing the condition. Thus, typically, an animal "at risk" of developing a condition is an animal present in an area where animals having the condition have been diagnosed and/or is likely to be exposed to a microbe causing the condition even if the animal has not yet manifested symptoms or signs of any condition caused by the microbe. Accordingly, administration of a composition can be performed before, during, or after the occurrence of the conditions described herein. Treatment initiated after the development of a condition may result in decreasing the severity of the symptoms of one of the conditions, or completely removing the symptoms. In this aspect, an "effective amount." is an amount effective to prevent the manifestation of symptoms of a disease, decrease the severity of the symptoms of a disease, and/or completely remove the symptoms.

Also provided are methods for decreasing colonization by microbes, for instance blocking the attachment sites of microbes, including tissues of the skeletal system (for instance, bones, cartilage, tendons and ligaments), muscular system, (for instance, skeletal and smooth muscles), circulatory system (for instance, heart, blood vessels, capillaries and blood), nervous system (for instance, brain, spinal cord, and peripheral nerves), respiratory system (for instance, nose, trachea lungs, bronchi, bronchioceles, alveoli), digestive system (for instance, mouth, salivary glands, esophagus, liver, stomach, large and small intestine), excretory system (for instance, kidneys, ureters, bladder and urethra), endocrine system (for instance, hypothalamus, pituitary, thyroid, pancreas and adrenal glands), reproductive system (for instance, ovaries, oviduct, uterus, vagina, mammary glands, testes, and seminal vesicles), lymphatic/immune systems (for instance, lymph, lymph nodes and vessels, mononuclear or white blood cells, such as macrophages, neutrophils, monocytes, eosinophils, basophils, and lymphocytes, including T cells and B cells), and specific cell lineages (for instance, precursor cells, epithelial cells, stem cells), and the like. The colonizing microbe may be a gram negative microbe, such as a member of the family Enterobacteriaceae, a member of the family Vibrionaceae, a member of the family Pseudomonadaceae, a member of the family Pasteurellaceae, and/or another gram negative microbes. In one embodiment the gram negative microbe may be *Salmonella* spp., such as *S. enterica* serovar, such as *S. enterica* serovar *Newport* or *S. enterica* serovar *Enteritidis*. The colonizing microbe may be a gram positive microbe, such as a member of the family Micrococcaceae, a member of the family Streptococcaceae, and/or another gram positive microbe.

Decreasing colonization in an animal may be performed prophylactically or, alternatively, can be initiated after the animal is colonized by the microbe. Treatment that is prophylactic—e.g., initiated before a subject is colonized by a microbe or while any colonization remains undetected—is referred to herein as treatment of a subject that is "at risk" of colonization by the microbe. Thus, typically, an animal "at risk" of colonization by a microbe is an animal present in an area where animals have been identified as colonized by the microbe and/or is likely to be exposed to the microbe even if the animal has not yet manifested any detectable indication of colonization by the microbe and regardless of whether the animal may harbor a subcolonization number of the microbe. Accordingly, administration of a composition can be performed before, during, or after the animal has first contact with the microbe. Treatment initiated after the animal's first contact with the microbe may result in decreasing the extent of colonization by the microbe, completely removing the microbe, and/or decreasing the likelihood that the animal becomes colonized by the microbe compared to an animal to which the composition is not administered. Thus, the method includes administering an effective amount of a composition described herein to an animal colonized by, or at risk of being colonized by, a microbe. Decreasing colonization refers to one or more of: decreasing the extent of colonization by the microbe, completely removing the microbe, and/or decreasing the likelihood that the animal becomes colonized by the microbe compared to an animal to which the composition is not administered. Methods for evaluating the colonization of an animal by a microbe are routine and known in the art. For instance, colonization of an animal's intestinal tract by a microbe can be determined by measuring the presence of the microbe in the animal's feces. It is expected that decreasing the colonization of an animal by a microbe will reduce transmission of the microbe to humans.

A composition described herein can be used to provide for active or passive immunization against bacterial infection. Generally, the composition can be administered to an animal to provide active immunization. However, the composition can also be used to induce production of immune products, such as antibodies, which can be collected from the producing animal and administered to another animal to provide passive immunity. Immune components, such as antibodies, can be collected to prepare compositions (preferably containing antibody) from serum, plasma, blood, colostrum, etc. for passive immunization therapies. Passive antibody compositions and fragments thereof e.g., scFv Fab, F(ab')$_2$ or Fv or other modified forms thereof, may be administered to a recipient in the form of serum, plasma, blood, colostrum, and the like. However, the antibodies may also be isolated from serum, plasma, blood, colostrum, and the like, using known methods for later use in a concentrated or reconstituted form such as, for instance, lavage solutions, impregnated dressings and/or topical agents and the like. Passive immunization preparations may be particularly advantageous for the treatment of acute systemic illness, or passive immunization of young animals that failed to receive adequate levels of passive immunity through maternal colostrum. Antibodies useful for passive immunization may also be useful to conjugate to various drugs or antibiotics that could be directly targeted to bacteria expressing during a systemic or localized infection a polypeptide present in a particle described herein or a polypeptide having an epitope structurally related to an epitope present on a polypeptide present in a particle described herein.

The present invention is illustrated by the following examples. It is to be understood that the particular examples, materials, amounts, and procedures are to be interpreted broadly in accordance with the scope and spirit of the invention as set forth herein.

Example 1

Materials and Methods

Polypeptides were extracted from *S. typhimurium* grown under iron-restricted conditions following the procedure described by Emery et al., (U.S. Pat. No. 6,432,412). The *S. typhimurium* strain was isolated from a commercial poultry facility. The polypeptide composition was supplied as an aqueous solution in Tris-buffered water at a concentration of 12,173 µg/mL. It was spray dried using a B-290 mini-spray dryer (Büchi LabortechniK AG) to produce insoluble microparticles. The spray drying was performed in open, sucking mode, with the aspirator set at 100%, sample pump at 18%, nitrogen flow rate 45 mm, inlet temperature at 120° C., outlet temperature approximately 57° C. and the high performance cyclone was used to collect the microparticles. When Imject Alum (Thermo Scientific) or saponin (Sigma Aldrich) were spray dried with the polypeptides, they were incorporated at 5% (w/w) with respect to the polypeptide antigen and spray dried under the same conditions as listed above.

The size of the particles was determined by Aveka Characterization Lab (St. Paul, Minn.) using a Horiba LA-950 laser scattering particle size distribution analyzer. The spray dried samples were suspended in water and sonicated for 1 minute in the analyzer to produce a monodisperse suspension prior to analysis.

Scanning electron microscopy was performed by the Imaging Center the University of Minnesota. Microparticles were mounted onto aluminum stubs with carbon double-sticky tabs and coated with 30 nm of gold/palladium using a Fullam EMS-76M sputter coater. Preparations were viewed using a Hitachi S3500N variable pressure scanning electron microscope. The instrument utilized Quartz PCI digital imaging software. Images were collected at an accelerating voltage of 5 kV and magnifications ranging from 300 to 6000 times.

Mouse studies were performed with CF-1 mice that were 16-22 g at the beginning of each study. Mice were vaccinated intraperitoneally with 0.2 mL of either spray dried *S. newport* derived polypeptides with an aluminum adjuvant (Imject alum, Thermo Scientific) or a standard aqueous *S. newport* derived polypeptides with an aluminum adjuvant (Imject alum). In both cases the adjuvant was present at 20% (v/v). The mice were injected with either 250 or 100 μg of polypeptide in each vaccine group. They were also boosted with the same vaccine 2 weeks vaccination and challenge was performed 4 weeks post-initial vaccination. The challenge organism, *S. newport*, was grown in tryptic soy broth overnight and 0.5 mL of the culture was added to 200 mL of tryptic soy broth in the morning. After approximately 4 hours of growth, the culture was centrifuged at 10,000 RPM for 10 minutes at 4° C. (Sorvall SL250 rotor). The culture was resuspended in cold saline to a concentration of $1 \times 10^{10}$ CFU's/mL. Each mouse received 200 μL of the challenge culture intraperitoneal. Mortality was recorded daily for 2 weeks post-challenge Free-LPS levels were determined by suspending 0.1 g of spray dried microparticles (see above) in 5.0 mL of sterile saline overnight at 4° C. After 14 hours the suspension was centrifuged at 10,000 RPM (SL-250 rotor, Sorvall) for 10 minutes. An equal amount of aqueous *S. typhimurium* derived polypeptide from the same lot was also centrifuged. The supernatants from both tubes were carefully removed and tested for endotoxin by Associates of Cape Cod using the gel-clot method.

Implants containing spray dried polypeptides were produced by combining insoluble microparticles with 2.5% (w/v) sodium alginate. The suspension was pumped into a two-fluid nozzle (Büchi LabortechniK AG, part number 044698) and nebulized with compressed nitrogen flowing at 25 mm (Cole Parmer, Model PMR1-010281. The microdroplets from the nebulized spray were directed at a stirred solution of 2.5% (w/v) $CaCl_2$. After 15 minutes of curing, a 0.5% (w/v) solution of xanthan gum was added to a final concentration of 0.16% (w/v) to prevent the microparticles from sedimenting. Microparticle suspensions were sized by Aveka Characterization Lab using a Horiba LA-950 laser scattering particle size distribution analyzer.

Poults were injected subcutaneously, day-of-age with 0.5 mL of microparticle suspensions (antigen amount ranging from 1000-100 μg), raised in a commercial turkey ban and bled at 8 weeks of age to assess the anti-*Salmonella* antibodies using an in-house developed ELISA. An Immulon 1B plate was coated, overnight at 4° C. with 1500 ng/well of *S. typhimurium* derived polypeptides in carbonate coating buffer (1.59 g/L sodium carbonate, 2.94 g/L sodium bicarbonate, pH 9.6). The plate was dumped out and blocked with 200 μl/well of 3% fish gelatin buffer (66.7 mL of 45% fish gelatin, Sigma Aldrich G7765-1L, into 1 L phosphate buffer, pH 7.4) for 1 hour at 37° C. with shaking at 100 RPM. After blocking, the plates were dumped out and 100 μL of the sera samples were added to the plate. Sera samples were diluted 1:1600 in 1.5% fish gelatin buffer prior to addition onto the plate. The plate was incubated for 1 hour at 37° C. with shaking at 100 RPM. Then, the plate was washed three times using a BioTek ELx404 plate washer. A stock solution of secondary antibody, goat anti-turkey horseradish peroxidase conjugate (KPL, 14-26-06, 0.05 mg/mL) was diluted 1:750 in 1.5% fish gelatin buffer and 100 μL was added to each well. The plate was incubated for 1 hour at 37° C. with shaking at 100 RPM. The plate was washed again three times and 100 μL of ABTS peroxidase substrate (KPL, 50-66-00) was added and incubated at 37° C. with shaking at 100 RPM for approximately 10 minutes. The absorbance in each well was read using a GENios plate reader (Tecan) at 405 nm and 490 nm.

Results

Figure 2:
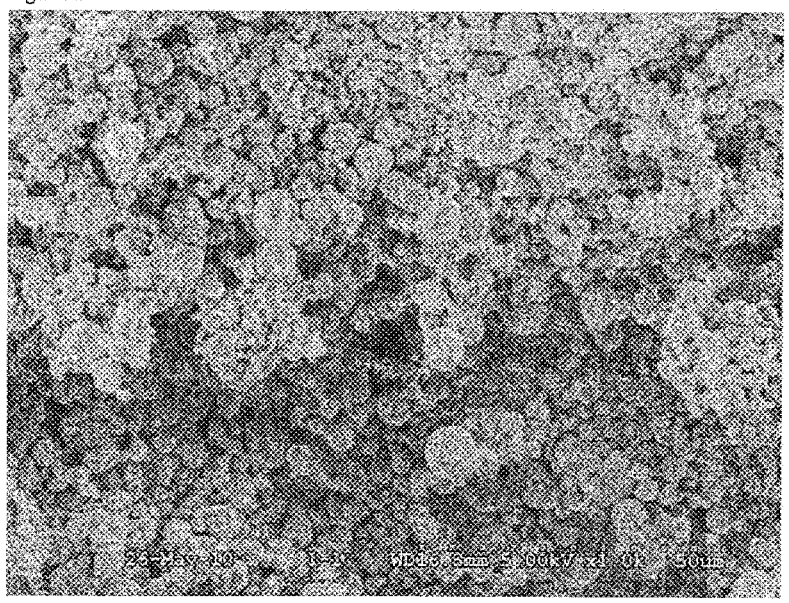
FIG. 2. Scanning electron microscopy image of spray dried S. typhimurium SRP particles. The scale bar is 50 micrometers.

Spray dried microparticles were insoluble in aqueous solutions. FIG. 1 shows the particle size analysis as measured by light scattering. As shown, the particles range in diameter from approximately 2-20 μm; with the average being about 8 μm. FIG. 2 shows a scanning electron micrograph of the spray dried microparticles. They are spherical microparticles.

Figure 3:
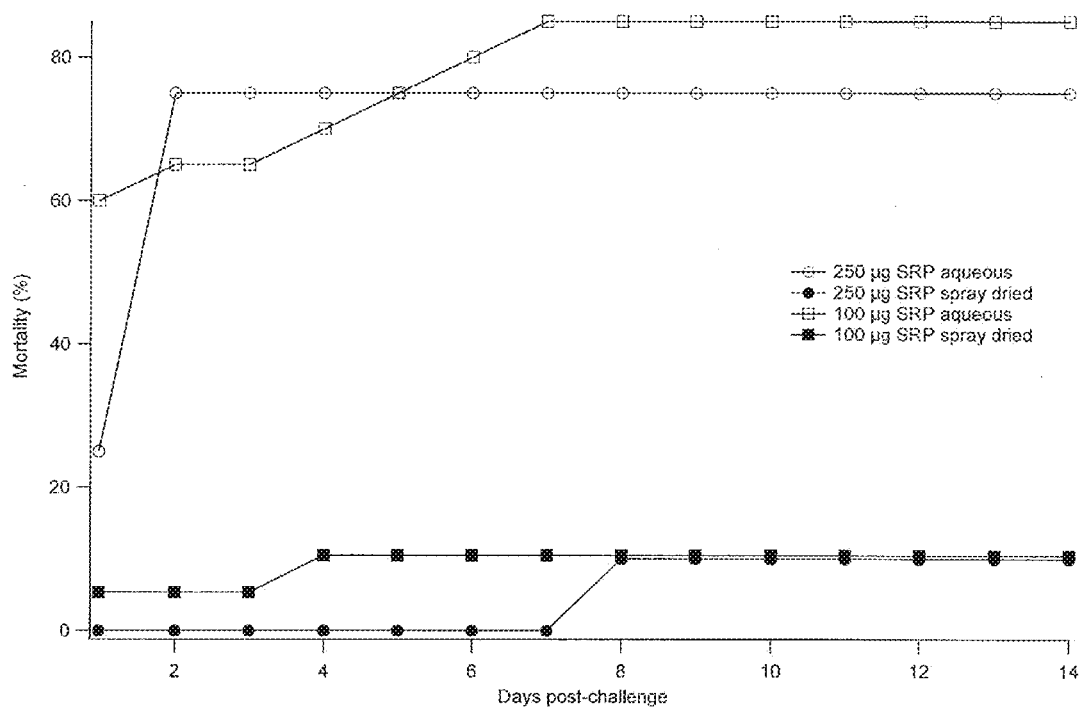
FIG. 3. Plot of daily mouse mortality after challenge with S. newport, illustrating the differences between spray dried (filled symbols) and aqueous (open symbols) SRP. Mice were injected with either 250 or 100 μg SRP and boosted at the same concentration 2 weeks later (circles and squares, respectively). The mice were challenged intraperitoneal with $1 \times 10^9$ colony-forming units and mortality monitored for 2 weeks.

Spray dried microparticles had higher immunogenicity than standard aqueous polypeptides alone. This can be shown by vaccinating mice with either spray dried microparticles or aqueous polypeptides and challenging with *S. newport*. FIG. 3 shows the cumulative daily mortality following intraperitoneal challenge with $1 \times 10^9$ CFU's of *S. newport*. At this challenge dose the mortality rate for unvaccinated mice was 100%. As shown, the groups receiving the spray dried polypeptides outperformed the standard aqueous polypeptides groups at 250 and 100 μg of antigen. This indicates that spray drying the extracted polypeptides into insoluble microparticles enhances the immunogenicity of the polypeptides.

Figure 4:
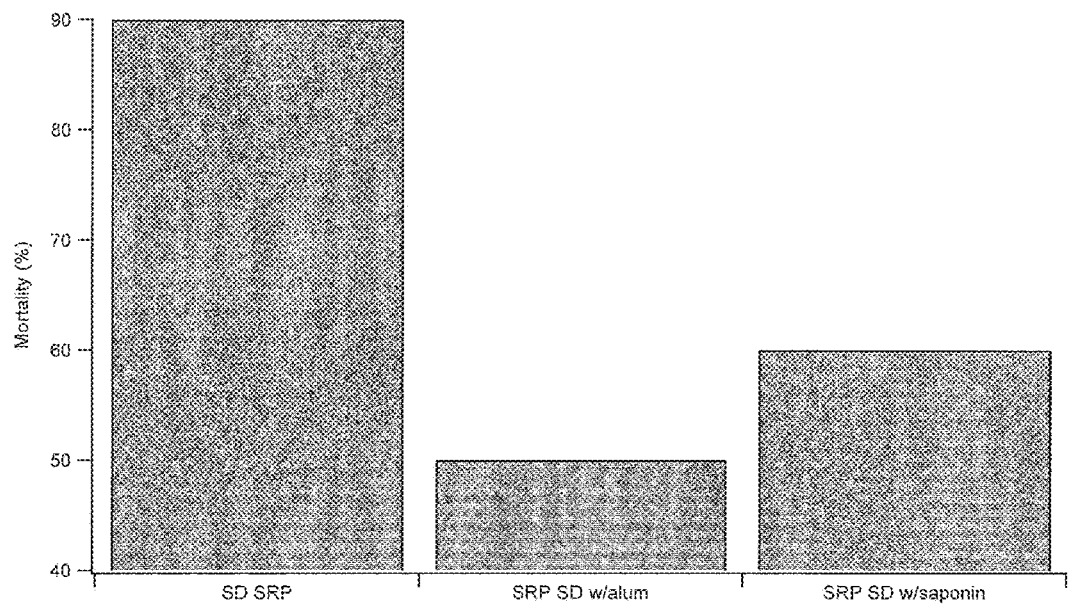
FIG. 4. Illustration of the differences between incorporating adjuvants into the SRP antigen before spray drying and SRP that was spray dried without any added adjuvants. Mice were vaccinated and boosted 2 weeks later with either spray dried SRP without any antigens (SD SRP), SRP spray dried with 5% (w/w) Imject alum (SD SRP w/alum) or SRP spray dried with 5% (w/w) saponin (SD SRP w/saponin). The mice were challenged intraperitoneal with $2.6 \times 10^8$ colony-forming units and mortality was monitored for 2 weeks.

In addition, adjuvants can be incorporated into the microparticles by spray drying the polypeptides with an adjuvant present. FIG. 4 illustrates the advantage of spray drying polypeptides with either an aluminum adjuvant or saponin. Mice that were injected with polypeptides that had been spray dried with 5% (w/w) Imject alum (Thermo Scientific) or with 5% (w/w) saponin (Sigma Aldrich) had less mortality after challenge with *S. newport* than mice injected with spray dried polypeptides without any adjuvants. This proves that incorporation of the adjuvant into the microparticle can increase its immunogenicity.

Spray drying bacterial-derived proteins such as siderophore receptor polypeptides and/or other iron acquisition polypeptides also has the benefit of reducing the free-LPS concentration in solution. For instance, Table 1 shows the concentrations of endotoxin found in aqueous polypeptides or the supernatants of spray dried polypeptides after incubation in saline at 4° C. for 14 hours.

TABLE 1

Endotoxin concentrations

| Sample | Endotoxin concentration (EU/mL) |
|---|---|
| Aqueous polypeptides | 125,000 |
| Spray dried polypeptides | 10,000 |

The spray drying process bound over 90% of the soluble LPS into the insoluble microparticles. This decrease in release of LPS from the particles was unexpected. This slow release of LPS is advantageous in that such decreased release of LPS may open up bacterial extract vaccines for use in species that are endotoxin sensitive.

Figure 5:
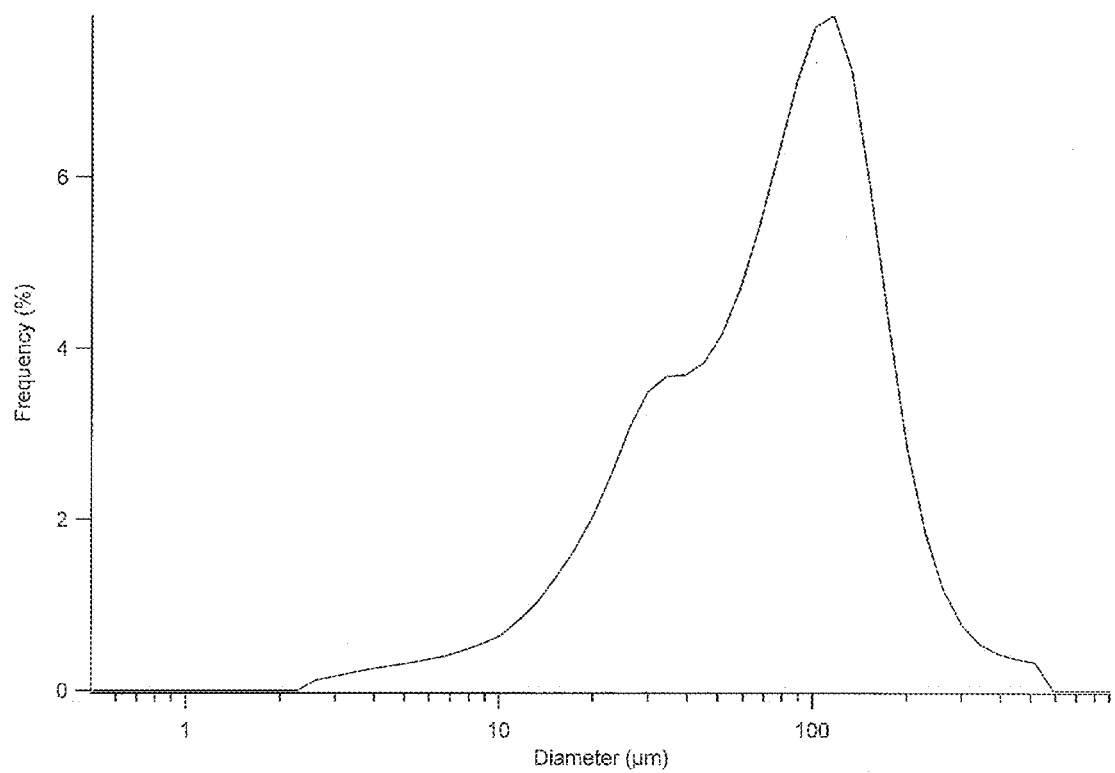
FIG. 5. Particle size distribution of alginate encapsulated spray dried SRP particles. The distribution plots the percentage of particles in the population with a given diameter.
Figure 6:
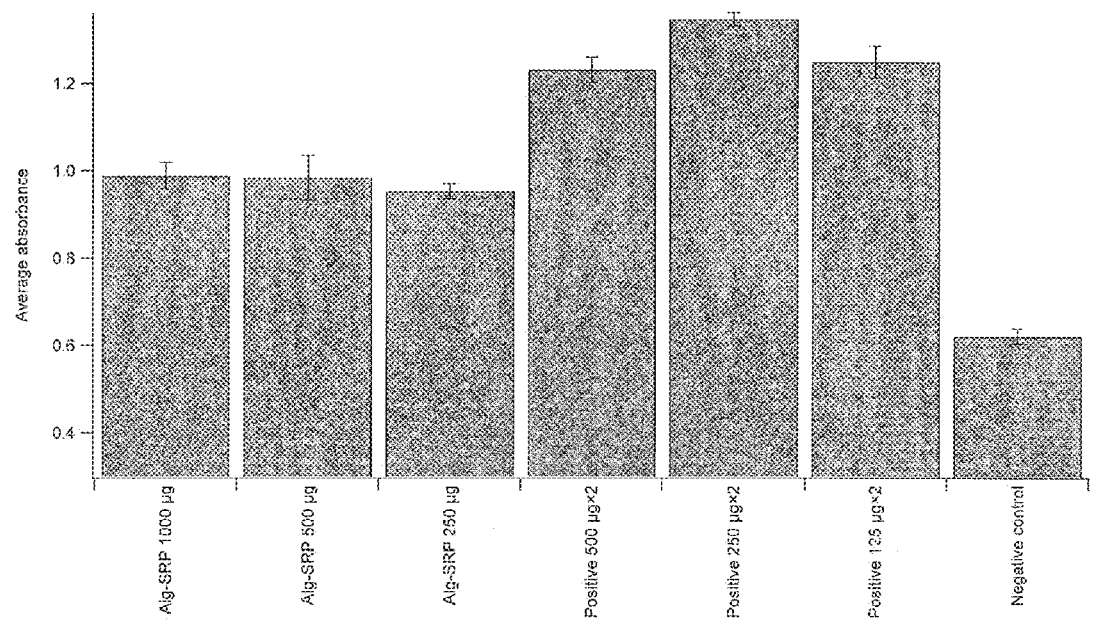
FIG. 6. Antibody responses to alginate encapsulated SRP injected day-of-age in turkey poults in comparison to turkeys vaccinated at 4 and 6 weeks with SRP mixed alum adjuvant and negative control turkeys. Alg-SRP, alginate encapsulated spray dried SRP polypeptides; positive, SRP polypeptides in alum adjuvant; ×2 refers to the injection of poults at 4 weeks and at 6 weeks with the SRP polypeptides in alum adjuvant.

Spray drying the polypeptides into insoluble microparticles also allows encapsulation of the polypeptides in a biodegradable matrix. For example, spray dried microparticles can be encapsulated in alginate, a biodegradable carbohydrate polymer. FIG. 5 shows the particle size distribution of the particles resulting from encapsulation of polypeptides with alginate. This formulation can be used as a delayed release vaccine. Day-of-age poults were injected with alginate encapsulated spray dried polypeptides and raised for 8 weeks. FIG. 6 displays the ELISA values for day-of-age injected turkeys in comparison with turkeys that had been injected at 4 and 6 weeks of age with polypeptides in an alum adjuvant. As shown, the day-of-age injected turkeys had significantly higher anti-*Salmonella* antibody levels than negative control turkeys that were raised in the same barn. Also, the day-of-age injected turkeys had comparable levels of anti-Salmonella antibodies in comparison to turkeys vaccinated and boosted with polypeptides. This clearly shows the use of alginate encapsulated, spray dried microparticles as a delayed release vaccine system.

Example 2

Particles were prepared as described above using polypeptides made by Epitopix, LLC (Willmar, Minn.) from *S. heidleberg* grown under iron-restricted conditions following the procedure described by Emery et al., (U.S. Pat. No. 6,432, 412). The particles (0.98 grams) were added to 100 mL of endotoxin free water (G-Biosciences, Product number 786-670). The particles were vigorously mixed and the first sample was collected immediately at t=0. The suspension was held at 4° C. Additional samples were removed at 1, 3, 5 and 26 hours. At each time point 3 mL were removed to measure solubility and 3 mL were removed to test endotoxin.

Figure 7:
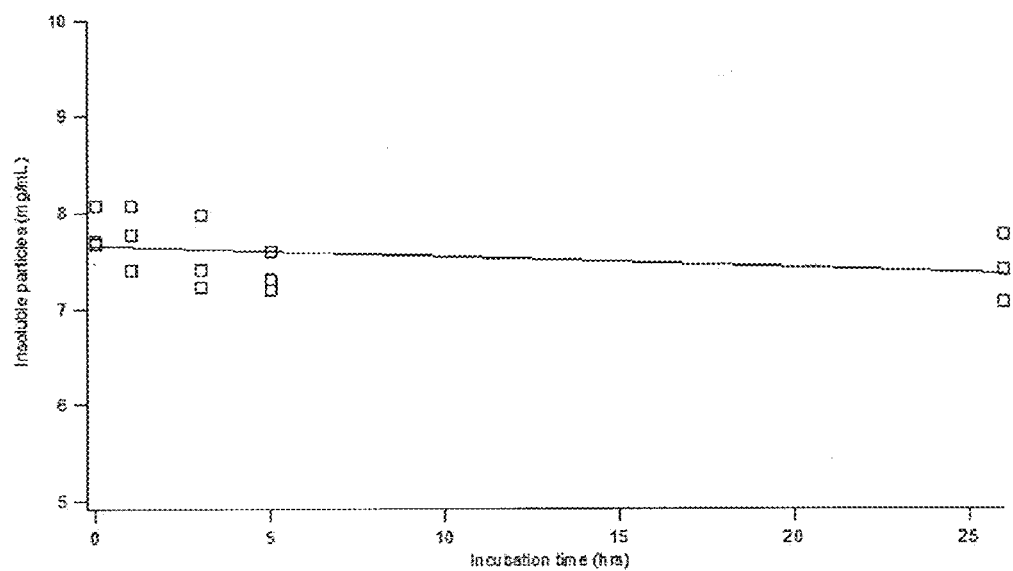
FIG. 7. Solubility of particles in water at 4° C.

The solubility was assessed by filtering the suspension through a pre-weighed and dried Whatman #3 filter. The filter was then heated to 70° C. for 24 hours and re-weighed. The results are shown in FIG. 7. There is very little solubilization following t=0; however, there appeared to be a burst of solubilization that occurred very rapidly. The expected concentration of SRP was 9.81 mg/mL based on the dry weight of the SRP powder and the volume of water added. This initial decrease in concentration may be due to salts that were spray dried with the SRP antigen.

Figure 8:
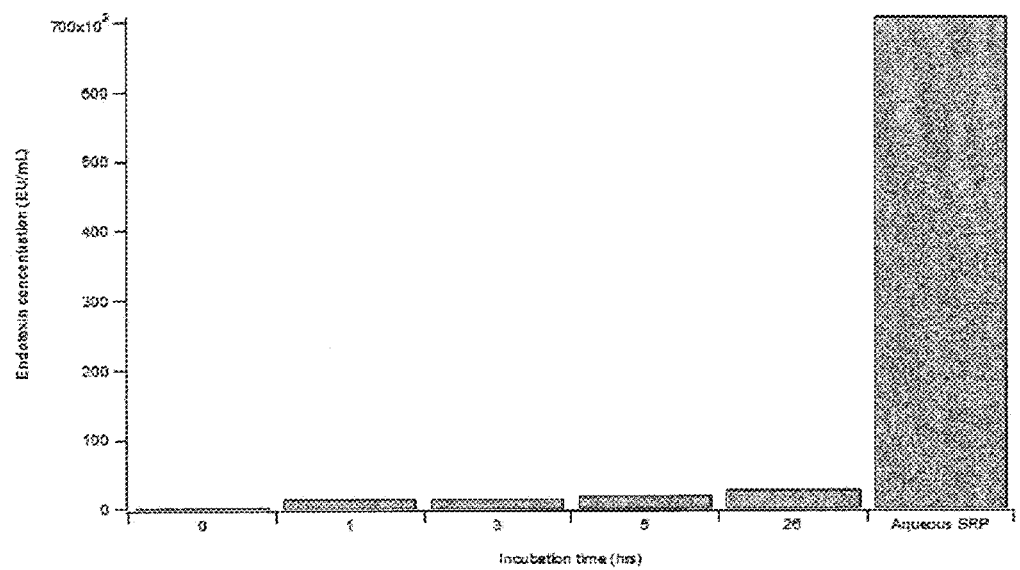
FIG. 8. Release of LPS by particles in water at 4° C.

For endotoxin testing, the 3 mL samples were centrifuged at 8,000×g for 10 minutes. The supernatant was carefully removed and stored in the refrigerator at 4° C. Endotoxin was measured by Associates of Cape Cod (East Falmouth, Mass.). The samples were compared to the same lot of *S. Newport* Bacterial Extract SRP that had not been spray dried and was matched to the spray dried SRP on a weight to weight basis. The results are shown in FIG. 8. The LPS present in the particles was released very slowly, resulting in a small increase in endotoxin levels in the solution with time. However, the amount of soluble endotoxin was 25 times less than in the aqueous SRP antigen.

The complete disclosure of all patents, patent applications, and publications, and electronically available material (including, for instance, nucleotide sequence submissions in, e.g., GenBank and RefSeq, and amino acid sequence submissions in e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for decreasing exposure of an animal to lipopolysaccharide comprising administering to an animal a composition comprising spray dried insoluble dry powder, wherein the spray dried insoluble dry powder comprise polypeptides obtained from a gram negative microbe and lipopolysaccharide, wherein solubility of the lipopolysaccharide in aqueous solution is reduced compared to solubility of lipopolysaccharide not present in the spray dried insoluble dry powder, wherein the powder comprises particles, and wherein the polypeptides are present at a concentration of at least 0.1 mg polypeptide/mg particles.

2. The method of claim 1 wherein the spray dried insoluble dry powder comprises the characteristic of releasing lipopolysaccharide at a rate of no greater than 10% EU/ml during the first 26 hours of incubating a sample of 1 gram of the spray dried insoluble dry powder in 100 mls of water at 4° C.

3. The method of claim 1 wherein the animal is an avian, a bovine, a caprine, an ovine, a porcine, a bison, an equine, a companion animal, a member of the family Cervidae, or a human.

4. The method of claim 3 wherein the avian is a chicken or a turkey.

5. The method of claim 2 wherein the equine is a horse.

6. The method of claim 3 wherein the companion animal is a dog or a cat.

7. The method of claim 1 wherein the animal is an embryo.

8. The method of claim 7 wherein the embryo is in ovo or in utero.

9. The method of claim 1 wherein the animal is between 1 day old and 6 weeks old.

10. The method of claim 1 wherein the animal is an adolescent or an adult.

11. The method of claim 1 wherein the composition further comprises a biocompatible degradable matrix.

12. The method of claim 11 wherein the spray dried insoluble dry powder is encapsulated in the biocompatible degradable matrix.

13. The method of claim 11 wherein the biocompatible degradable matrix comprises alginate.

14. The method of claim 1 wherein the composition further comprises an adjuvant.

15. The method of claim 1 wherein the spray dried insoluble dry powder further comprises an adjuvant.

16. The method of claim 1 wherein the polypeptides comprise a microbial outer membrane polypeptide, a microbial porin polypeptide, or a combination thereof.

17. The method of claim 1 wherein the gram negative microbe is a member of the family Enterobacteriaceae, a member of the family Vibrionaceae, a member of the family Pasteurellaceae, or a member of the family Pseudomonadaceae.

18. The method of claim 16 wherein the microbial outer membrane polypeptide is an iron acquisition polypeptide.

19. The method of claim 18 wherein the iron acquisition polypeptide has a molecular weight of between 60 kDa and 100 kDa as determined by sodium dodecyl-polyacrylamide gel electrophoresis.

20. The method of claim 16 wherein the porin polypeptide has a molecular weight of between 30 kDa and 43 kDa as determined by sodium dodecyl-polyacrylamide gel electrophoresis.

21. The method of claim 1 wherein the spray dried insoluble dry powder further comprises a carrier.

22. The method of claim 21 wherein the carrier comprises zein.

23. The method of claim 21 wherein the carrier is present at no greater than 0.001 mg carrier/mg powder.

24. The method of claim 21 wherein the carrier is present at a ratio of carrier to polypeptide (weight:weight) of no greater than 0.05:1.

25. The method of claim 1 wherein the composition comprises a pharmaceutically acceptable excipient.

* * * * *